US011707520B2

(12) United States Patent
Rappuoli et al.

(10) Patent No.: US 11,707,520 B2
(45) Date of Patent: *Jul. 25, 2023

(54) ADJUVANTED VACCINES WITH NON-VIRION ANTIGENS PREPARED FROM INFLUENZA VIRUSES GROWN IN CELL CULTURE

(71) Applicant: Seqirus UK Limited, Berkshire (GB)

(72) Inventors: Rino Rappuoli, Siena (IT); Derek O'Hagan, Siena (IT); Giuseppe Del Giudice, Siena (IT)

(73) Assignee: Seqirus UK Limited, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/072,136

(22) Filed: Oct. 16, 2020

(65) Prior Publication Data

US 2021/0170021 A1 Jun. 10, 2021

Related U.S. Application Data

(63) Continuation of application No. 12/092,325, filed as application No. PCT/GB2006/004128 on Nov. 6, 2006, now Pat. No. 10,842,867.

(60) Provisional application No. 60/735,658, filed on Nov. 11, 2005, provisional application No. 60/734,028, filed on Nov. 3, 2005.

(51) Int. Cl.
*A61K 39/145* (2006.01)
*A61K 39/39* (2006.01)
*A61K 39/12* (2006.01)
*A61K 39/00* (2006.01)

(52) U.S. Cl.
CPC ............. *A61K 39/39* (2013.01); *A61K 39/12* (2013.01); *A61K 39/145* (2013.01); *A61K 2039/55561* (2013.01); *A61K 2039/55566* (2013.01); *A61K 2039/55572* (2013.01); *A61K 2039/57* (2013.01); *C12N 2760/16134* (2013.01); *C12N 2760/16234* (2013.01)

(58) Field of Classification Search
CPC ........ A61K 2039/55566; A61K 39/145; A61K 2039/5252; A61K 9/107; A61K 2039/55572; C12N 7/00; C12N 2760/16134; C12N 2760/16234; C12N 2760/16151; C12N 2760/16034; C12N 2760/16251; C12N 2760/16171; C12N 2710/10334; C12N 2760/18734; C12N 2770/20034; C12N 2760/16111; A61P 31/16

See application file for complete search history.

(56) References Cited

U.S. PATENT DOCUMENTS

| | | |
|---|---|---|
| 4,500,513 A | 2/1985 | Brown et al. |
| 5,750,110 A | 5/1998 | Prieels et al. |
| 5,762,939 A | 6/1998 | Smith et al. |
| 5,776,468 A | 7/1998 | Hauser |
| 5,824,536 A | 10/1998 | Webster et al. |
| 5,948,410 A | 9/1999 | Van Scharrenburg et al. |
| 6,136,321 A | 10/2000 | Barrett et al. |
| 6,245,532 B1 | 6/2001 | Smith et al. |
| 6,299,884 B1 | 10/2001 | Van Nest et al. |
| 6,372,223 B1 | 4/2002 | Kistner et al. |
| 6,372,227 B1 | 4/2002 | Garcon et al. |
| 6,506,386 B1 | 1/2003 | Friede et al. |
| 6,544,518 B1 | 4/2003 | Friede et al. |
| 6,861,410 B1 | 3/2005 | Ott et al. |
| 6,951,754 B2 | 10/2005 | Hoffman |
| 7,316,813 B2 | 1/2008 | Eichhorm |
| 7,357,936 B1 | 4/2008 | Garcon |
| 7,384,642 B2 | 6/2008 | Minke et al. |
| 7,425,336 B2 | 9/2008 | Minke et al. |
| 7,641,911 B2 | 1/2010 | Ott et al. |
| 7,959,931 B2 | 6/2011 | Colegate et al. |
| 8,206,749 B1 | 6/2012 | O'Hagan et al. |
| 8,309,139 B2 | 11/2012 | O'Hagan et al. |
| 8,506,966 B2 | 8/2013 | Podda et al. |
| 8,808,686 B2 | 8/2014 | Del Giudice et al. |
| 8,895,629 B2 | 11/2014 | Rueckl et al. |
| 9,278,126 B2 * | 3/2016 | Contorni ............. A61K 39/145 |
| 9,566,326 B2 * | 2/2017 | Podda .................... A61P 31/12 |
| 9,669,088 B2 * | 6/2017 | Podda .................... A61K 39/12 |
| 9,821,051 B1 * | 11/2017 | Groth .................... A61K 47/26 |
| 9,901,630 B2 * | 2/2018 | Del Giudice ........... A61P 31/16 |
| 10,113,795 B2 * | 10/2018 | Hoffman, Jr. ............. F26B 3/30 |
| 10,149,901 B2 * | 12/2018 | Contorni ............. A61K 39/145 |
| 10,843,867 B2 * | 11/2020 | Rossomando ..... B65D 85/8043 |
| 10,946,088 B2 * | 3/2021 | Haussmann ............ A61P 31/12 |

(Continued)

FOREIGN PATENT DOCUMENTS

| | | |
|---|---|---|
| CA | 2601022 | 9/2006 |
| EP | 0 864 646 | 9/1998 |

(Continued)

OTHER PUBLICATIONS

European Search Report issued in European Patent Application No. 20160713.2, dated Aug. 10, 2020, mailed from the European Patent Office, 11 pages.

(Continued)

*Primary Examiner* — Bao Q Li

(74) *Attorney, Agent, or Firm* — Finnegan, Henderson, Farabow, Garrett & Dunner, LLP

(57) ABSTRACT

An immunogenic composition comprising: (i) a non-virion influenza virus antigen, prepared from a virus grown in cell culture; and (ii) an adjuvant. Preferred adjuvants comprise oil-in-water emulsions.

20 Claims, 4 Drawing Sheets

(56) References Cited

U.S. PATENT DOCUMENTS

| | | | |
|---|---|---|---|
| 11,246,921 B2* | 2/2022 | Contorni | A61P 31/16 |
| 11,406,701 B2* | 8/2022 | Del Giudice | A61P 37/04 |
| 2003/0147898 A1 | 8/2003 | Van Nest et al. | |
| 2004/0081686 A1 | 4/2004 | Kravtzoff et al. | |
| 2004/0096463 A1 | 5/2004 | Garcon et al. | |
| 2004/0109874 A1 | 6/2004 | Chen et al. | |
| 2004/0241187 A1 | 12/2004 | Eichhorn | |
| 2005/0123599 A1 | 6/2005 | Ott et al. | |
| 2005/0287127 A1 | 12/2005 | Yang et al. | |
| 2006/0115489 A1 | 6/2006 | Birkett et al. | |
| 2006/0188977 A1 | 8/2006 | Schwartz | |
| 2007/0048819 A1 | 3/2007 | Minke et al. | |
| 2007/0048821 A1 | 3/2007 | Minke et al. | |
| 2007/0116709 A1 | 5/2007 | O'Hagan et al. | |
| 2007/0141078 A1 | 6/2007 | D'Hondt et al. | |
| 2007/0298093 A1 | 12/2007 | Konur et al. | |
| 2008/0181911 A1 | 7/2008 | Hanon et al. | |
| 2008/0254065 A1 | 10/2008 | Podda et al. | |
| 2009/0060950 A1 | 3/2009 | Kistner et al. | |
| 2009/0202590 A1 | 8/2009 | Colegate et al. | |
| 2009/0220545 A1 | 9/2009 | Del Giudice et al. | |

FOREIGN PATENT DOCUMENTS

| | | |
|---|---|---|
| JP | 62201573 | 9/1987 |
| WO | WO 90/14837 A1 | 12/1990 |
| WO | WO 95/17209 | 6/1995 |
| WO | WO 9517210 A | 6/1995 |
| WO | WO 96/15231 | 5/1996 |
| WO | WO 96/33739 | 10/1996 |
| WO | WO 96/37624 | 11/1996 |
| WO | WO 97/37001 | 10/1997 |
| WO | WO 98/15287 | 4/1998 |
| WO | WO 98/16247 | 4/1998 |
| WO | WO 98/40100 | 9/1998 |
| WO | WO 98/56414 | 12/1998 |
| WO | WO 98/57659 | 12/1998 |
| WO | WO 98/57660 | 12/1998 |
| WO | WO 9856414 | 12/1998 |
| WO | WO 99/11241 | 3/1999 |
| WO | WO 99/27961 | 6/1999 |
| WO | WO 01/80836 | 4/2000 |
| WO | WO 00/60050 A2 | 10/2000 |
| WO | WO 00/62800 | 10/2000 |
| WO | WO 06/2800 A1 | 10/2000 |
| WO | WO 0060050 A1 | 10/2000 |
| WO | WO 01/04333 A1 | 1/2001 |
| WO | WO 01/21151 A1 | 3/2001 |
| WO | WO 01/21152 | 3/2001 |
| WO | WO 01/21207 | 3/2001 |
| WO | WO 01/22992 | 4/2001 |
| WO | WO 01/22992 A2 | 4/2001 |
| WO | WO 02/32450 | 4/2002 |
| WO | WO 02/32454 | 4/2002 |
| WO | WO 02/097072 | 12/2002 |
| WO | WO 00/15251 A2 | 3/2003 |
| WO | WO 2004/058142 | 7/2004 |
| WO | WO 2004/084937 | 10/2004 |
| WO | WO 2004/098509 | 11/2004 |
| WO | WO 2005/009462 | 2/2005 |
| WO | WO 2005/107797 | 11/2005 |
| WO | WO 2005/117958 | 12/2005 |
| WO | WO 2006/060710 | 6/2006 |
| WO | WO 2006/100109 | 9/2006 |
| WO | WO 2006/100110 | 9/2006 |
| WO | WO 2006/100111 | 9/2006 |
| WO | WO 2007/006939 A2 | 1/2007 |
| WO | WO 2007/008939 A2 | 1/2007 |
| WO | WO 2008/032219 | 3/2008 |
| WO | WO 2008/128939 A1 | 10/2008 |

OTHER PUBLICATIONS

Moran et al., "Th2 Responses to Inactivated Influenza Virus Can Be Converted to Th1 Responses and Facilitate Recovery from Heterosubtypic Virus Infection," The Journal of Infectious Diseases, 1999, 180, pp. 579-585.

Lu, "Relative effectiveness of cell-cultured versus egg-based influenza vaccines, 2017-18," ACIP meeting presentation, Jun. 20, 2018, 19 pages.

FDA statement dated Feb. 15, 2018, 4 pages.

FDA statement dated Sep. 27, 2018, 5 pages.

Martinez-Sobrido et al., "Generation of Recombinant Influenza Virus from Plasmid DNA," Journal of Visualized Experiments, 2010, 42, doi:10.3791/2057, 5 pages.

Anderson et al., (2010), "Physicochemical characterization and biological activity of synthetic TLR4 agonist formulations," Colloids Surf B Biointerfaces, 75(1):123-32.

Assessment Report for Celvapan (Oct. 1, 2009) Doc. Ref: EMEA/CHMP/629184/2009.

Babiuk et al., "Aggregate content influences the Th1/Th2 immune response to influenza vaccine: evidence from a mouse model," J Med Virol, 72(1):138-142, (2004).

Barchfeld et al., "Enhancement of humoral response against human influenza vaccine with the simple submicron oil/water emulsion adjuvant MF59," Vaccine 13, 1557-62, Nov. 1995.

Baudner et al., "MF59 emulsion is an effective delivery system for a synthetic TLR4 agonist (E6020)," Pharm Res, 26(6):1477-85, (2009).

Bordi et al., "Salt-induced aggregation in cationic liposome aqueous suspensions resulting in multi-step self-assembling complexes," Colloids and Surfaces B: Biointerfaces, 26(4):341-350, (2002).

Chattaraj et al., "Biodegradable microparticles of influenza viral vaccine: comparison of the effects of routes of administration on the in vivo immune response in mice," J Control Release, 58(2):223-232, (1999).

Clegg et al., "Adjuvant solution for pandemic influenza vaccine production," Proc Natl Acad Sci USA, 109(43):17585-90, (2012).

de Wit et al., "Protection of mice against lethal infection with highly pathogenic H7N7 influenza A virus by using a recombinant low-pathogenicity vaccine strain", J Virol, 79(19):12401-12407, (2005).

Dooley et al., "Adjuvanted Influenza vaccine," BioDrugs, 14(1):61-9, (2000).

English translation of Japanese Inquiry dated Feb. 25, 2014, for JP App. No. 2008-536453, 6 pages.

English translation of Japanese Notice of Reasons for Rejection dated Dec. 19, 2011, for JP App, No. 2008-538453, 8 pages.

European Search Report, dated Mar. 14, 2013, for European Application No. 11162713.9, filed Nov. 6, 2006, 6 pages.

Evans et al. (2003). "Enhancement of antigen-specific immunity via the TLR4 ligands MPL adjuvant and Ribl.529," Expert Rev Vaccines, 2(2):219-29.

Fedson (2005), "Preparing for pandemic vaccination; an international policy agenda for vaccine development," J Public Health Policy, 26(1):4-29.

Franca de Barros Jr. et al., "Characterization of sialidase from an influenza A (H3N2) virus strain : kinetic parameters and substrate specificity", Intervirology, 46(4):199-206, (2003).

Galarza et al., "Virus-like particle (VLP) vaccine conferred complete protection against a lethal influenza virus challenge," Viral Immunol, 18(2):365-372, (2005).

Gonzalez et al., "Safety and immunogenicity of a pediatric vaccine presentation of an influenza vaccine", 2000, Archives of Disease in Childhood, vol. 83, pp. 488-491.

Halperin et al., "Safety and immunogenicity of a new influenza vaccine grown in mammalian cell culture," Vaccine, 16(13): 1331-1335, (1998).

Hauge et al., "The immunogenicity of a cell-derived H7N1 split influenza virion vaccine in mice," Scand J Immunol, 69(6):576-8, (2009).

Ichinohe et al., "Synthetic double-stranded RNA poly(1:C) combined with mucosal vaccine protects against influenza virus infection," J Virol, 79(5):2910-2919, (2005).

International Search Report and Written Opinion for International Application No. PCT/GB2006/004128, dated May 6, 2008.

(56) References Cited

OTHER PUBLICATIONS

International Search Report and Written Opinion for International Application No. PCT/GB2006/004139, dated May 6, 2008.
International Search Report and Written Opinion for International Application No. PCT/IB2006/003658, dated May 6, 2008.
Kasturi et al., "Programming the magnitude and persistence of antibody responses with innate immunity," Nature, 470(7335):543-547, (2011).
Kistner et al., "A whole virus pandemic influenza H1N1 vaccine is highly immunogenic and protective in active immunization and passive protection mouse models," PLoSOne, 5(2):e9349, (2010).
Klinman, "Immunotherapeutic uses of CpG oligodeoxynucleotides," Nat Rev Immunol, 4(4):249-258, (2004).
Krieg, "CpG motifs: the active ingredient in bacterial extracts?" Nat Med, 9(7):831-835, (2003).
Minutello et al., "Safety and immunogenicity of an inactivated subunit influenza virus vaccine combined with MF59 adjuvant emulsion in elderly subjects, immunized for three consecutive influenza seasons," Vaccine, 17(2):99-104, (1999).
Moldoveanu et al., "CpG DNA, a novel immune enhancer for systemic and mucosal immunization with influenza virus," Vaccine, 16(11-12):1216-1224, (1998).
Novartis Vaccines and Diagnostics (Aug. 2009). "FCC H1 N1sw Vaccine, Module 2", Retrieved Jul. 16, 2014 from <http://www.mhlw.go.jp/shingi/201 0/01 /dl/s0115-7z.pdf.
O'Kistner et al., Vaccine, vol. 16, Issues 9-10, pp. 960-968 (1998).
Singh et al., "A novel bioadhesive intranasal delivery system for inactivated influenza vaccines," J Control Release, 70(3):267-276, (2001).
Singh et al., "Cationic microparticles are an effective delivery system for immune stimulatory cpG DNA," Pharm Res, 18(10): 1476-1479, (2001).
Stills, "Adjuvants and antibody production: dispelling the myths associated with Freund's complete and other adjuvants," Ilar J, 46(3):280-93, (2005).
U.S. Appl. No. 12/092,325, filed Sep. 26, 2008; Final Office Action dated Aug. 26, 2015.
U.S. Appl. No. 12/092,325, filed Sep. 26, 2008; Final Office Action dated Nov. 18, 2010.
U.S. Appl. No. 12/092,325, filed Sep. 26, 2008; Non-Final Office Action dated Aug. 15, 2013.
U.S. Appl. No. 12/092,325, filed Sep. 26, 2008; Non-Final Office Action dated Dec. 15, 2009.
U.S. Appl. No. 12/092,325, filed Sep. 26, 2008; Non-Final Office Action dated Feb. 13, 2015.
U.S. Appl. No. 12/092,325, filed Sep. 26, 2008; Non-Final Office Action dated Jun. 21, 2016.
U.S. Appl. No. 12/092,325, filed Sep. 26, 2008; Non-Final Office Action dated Jun. 26, 2014.
U.S. Appl. No. 12/092,325, filed Sep. 26, 2008; Non-Final Office Action dated Nov. 29, 2013.
U.S. Appl. No. 12/092,325, filed Sep. 26, 2008; Restriction Requirement dated Jun. 24, 2010.
U.S. Appl. No. 14/574,207, filed Dec. 17, 2014; Non-Final Office Action dated Aug. 25, 2016.
U.S. Appl. No. 14/574,207, filed Dec. 17, 2014; Non-Final Office Action dated Aug. 27, 2015.
U.S. Appl. No. 14/574,207, filed Dec. 17, 2014; Restriction Requirement dated Apr. 1, 2015.
Ulmer et al., "Vaccine manufacturing: challenges and solutions," Nat Biotechnol, 24(11):1377-1383, (2006).
U.S. Final Office Action dated May 5, 2015, for U.S. Appl. No. 13/148,939, filed Dec. 15, 2011.
U.S. Office Action dated Sep. 23, 2014, for U.S. Appl. No. 13/148,939, filed Dec. 15, 2011.
Valensi et al., "Systemic cytokine profiles in BALB/c mice immunized with trivalent influenza vaccine containing MF59 oil emulsion and other advanced adjuvants," J Immunol, 153(9):4029-39, (1994).
Vanlandschoot et al., "Recombinant secreted haemagglutinin protects mice against a lethal challenge of influenza virus," Vaccine, 11(12):1185-7, (1993).
Vasilakos et al., "Adjuvant activities of immune response modifier R-848: comparison with CpG ODN," Cell Immunol, 204(1):64-74, (2000).
Vermout et al., "Choix d'un adjuvant lors d'essais de vaccination," Ann. Med. Vet., 147:393-401, (2003).
Weeratna et al., "CpG DNA induces stronger immune responses with less toxicity than other adjuvants," Vaccine, 18(17):1755-62, (2000).
Weeratna et al., "TLR agonists as vaccine adjuvants: comparison of CpG ODN and Resiquimod (R-848)," Vaccine, 23(45):5263-70, (2005).
Willian Egan, Testimony published by United States of Department of Health & Human Services, Oct. 5, 2004.
Woodhour et al., "Development and application of new parenteral adjuvants. V. Comparative potencies of influenza vaccines emulsified in various oils," J. Immunol., 86:681-89, (1961).
Assessment Report for Celvapan, Doc. Ref: EMEA/CHMP/629184/ 2009 (2009).
BASF, "Pluronic L121 BLock Copolymer Surfatnat,"Technical Bulletin, 1 page (2004).
Berger, "Science commentary; Th1 and Th2 responses: what are they?" BMJ, 321:424, 1 page (2000).
Bresson et al., "Safety and immunogenicity of an inactivated split-virion influenzaAiVietnam/1194/2004 (H5N1) vaccine: phase 1 randomised trial," Lancet 367, pp. 1657-1664 (2006).
Canada Communicable Disease Report, vol. 27 (ACS-4) (2001).
Couch et al., "Superior antigen-specific CD4+ T-cell response with AS03-adjuvantation of a trivalent influenza vaccine in a randomised trial of adults aged 65 and older," BMC Infectious Diseases, vol. 14:425 (2014) (14 pages).
Danihelkova et al., "Disruption of influenza virus A by diethylether-Tween and tri-N-butyl phosphate-Tween mixtures," Acta Virologica 28(1), pp. 26-32 (1984).
Egan, William, Testimony published by FDAm United States of Department of Health & Human Services (2004).
Emmie de Wit et al., J. Virol., vol. 79, No. 9, pp. 12401-12407 (2005).
European Medicines Agency, "Celvapan, International nonproprietary name: Pandemic influenza vaccine (H5N1) (whole virion, vero cell derived, inactivated)," Assessment Report, pp. 1-11 (2009).
European Medicines Agency, "Pumarix, Common name: Pandemic influenza vaccine (H5N1) (split viron, inactivated, adjuvated)," Assessment Report, pp. 1-75 (2011).
European Office Action dated Jul. 8, 2015, in application No. EP 11159208.5, 7 pages.
Geier et al., "Influenza vaccination and Guillain Barre Syndrome,"Clinical Immunology 107; pp. 116-121 (2003).
He et al., "Calcium Phosphate Nanoparticle Adjuvant," Clinical and Diagnostic Laboratory Immunology 7(6):899-903 (2000).
Health Canada, health Products and Food Branch, "AREPANRIX™ H1N1, AS03-Adjuvated H1 N Pandemic Influenza Vaccine," Summary basis of decision (SBD), pp. 1-14 (2010).
Horimoto and Kawaoka, "Influenza: Lessons from past pandemics, warnings from current incidents," Nat. Rev. Microbiol. 3(8), pp. 591-600 (2005).
Johannsen et al., "The quantification of the haemagglutinin content of influenza whole virus and Tween-ether split vaccines," Journal of Biological Standardization 911 (4); pp. 341-352 (1983).
Lindblad, "Aluminum compounds for use in vaccine," Immunology and Cell Biology 82:497-505 (2004).
National Advisory Committee on Immunization, "Statement on Influenza Vaccine," Canada Communicable Disease Report, Advisory Committee Statement, vol. 27, DCC-4, 24 pages (2001).
Nicholson et al., "Safety and antigenicity of non-adjuvanted and MF59-adjuvanted influenza A/Duck/Singapore/97 (H5N3) vaccine: a randomised trial of two potential vaccines against H5N1 influenza," Lancet 357(9727; pp. 1937-1943 (2001).
Nony et al., "Impact of osmolality on burning sneations during and immediately after intramuscular infection of 0.5 ml of vaccine suspensions in healthy adults," Vaccine 19, pp. 3645-3651 (2001).

(56) References Cited

OTHER PUBLICATIONS

O'Hagan et al., "Vaccine Adjuvants: Preparation Methods and Research Protocols," Humana Press, only chapter 12; pp. 211-228 (2000).
Ott et al., "MF59. Design and evaluation of a safe and potent adjuvant for human vaccines," Pharm Biotechnol. 6, pp. 277-296 (1995).
Scheifele et al., "Ocular and respiratory symptoms attributable to inactivated split influenza vaccine: Evidence from a controlled trial involving adults," Clinical Infectious Diseases 36; pp. 850-857 (2003).
Schuind et al., "Immunogenicity and Safety of an EB66 Cell-Culture-Derived Influenza A/Indonesia/5/2005 (H5N1) AS03-Adjuvanted Vaccine: A Phase 1 Randomized Trial," Journal of Infectious Diseases 212(4):531-541 (2015).
Skowronski et al., "Does antigen-specific cytokine response correlate with the experience of oculorespiratory syndrome after influenza vaccine?," J. Infect. Dis. 187(3); pp. 495-499 (2003).
Statement of Grounds of Appeal, filed in relation to EP1951301, dated Nov. 30, 2012, 8 pages.
Toews et al., "Mass spectrometric identification of formaldehyde-induced peptide modifications under in vivo protein cross-linking conditions," Analytica Chemica Acta 618; pp. 168-183 (2008).
Weller et al., "Split virus influenza vaccination in children: an evaluation of efficacy," Current Medical Research and Opinion, vol. 9, No. 10, pp. 713-715 (1985).
Wood et al., "Experience with the clinical development of influenza vaccines for potential pandemics," Meo. Microbiol. Immunol. 191; pp. 197-201 (2002).
World Health Organization, "Recommendations for production and control of influenza vaccine (inactivated)," 33 pages (2003).
U.S. Appl. No. 12/092,131, filed Dec. 5, 2008; Restriction Requirement dated Jul. 29, 2009 (5 pages).
U.S. Appl. No. 12/092,131, filed Dec. 5, 2008; Non-Final Office Action dated Dec. 16, 2009 (17 pages).
U.S. Appl. No. 12/092,131, filed Dec. 5, 2008; Restriction Requirement dated Jul. 8, 2010 (5 pages).
U.S. Appl. No. 12/092,131, filed Dec. 5, 2008; Final Office Action dated Dec. 29, 2010 (10 pages).
U.S. Appl. No. 12/092,131, filed Dec. 5, 2008; Non-Final Office Action dated Sep. 25, 2013 (20 pages).
U.S. Appl. No. 12/092,131, filed Dec. 5, 2008; Non-Final Office Action dated May 16, 2014 (31 pages).
U.S. Appl. No. 12/092,131, filed Dec. 5, 2008; Non-Final Office Action dated Feb. 5, 2015 (32 pages).
U.S. Appl. No. 12/092,131, filed Dec. 5, 2008; Final Office Action dated Oct. 6, 2015 (27 pages).
U.S. Appl. No. 12/092,131, filed Dec. 5, 2008; Non-Final Office Action dated Aug. 26, 2016 (32 pages).
CenterWatch published by FDA (Flaud News FDA Drug Approval copy right 1995-2016, p. 1-2), searched by 2016.
Bruhl et al., Vaccine, 2000, vol. 19, pp. 1149-1158.
Neirynck et al. (Nature Medicine 1999, vol. 5, pp. 1157-1163.
Altaner et al. (1993). "Envelope glycoprotein gp51 of bovine leukemia virus is differently glycosylated in cells of various species and organ origin," Vet Immunol Immunopathol. 36(2):163-77.
Gambaryan et al. (1998). "Effects of host-dependent glycosylation of hemagglutinin on receptor-binding properties on H1N1 human influenza A virus grown in MDCK cells and in embryonated eggs," Virology. 247(2):170-7.
Higgins et al. (1996). "MF59 adjuvant enhances the immunogenicity of influenza vaccine in both young and old mice," Vaccine, 14(6):478-84.
Lin et al. (2013). "Different immunity elicited by recombinant H5N1 hemagglutinin proteins containing pauci-mannose, high-mannose, or complex type N-glycans," PLoS One. 8(6):e66719.
O'Hagan et al. (2011). "MF59 adjuvant: the best insurance against influenza strain diversity," Expert Rev Vaccines, 10(4):447-62.

Ott et al. (1995). "Enhancement of humoral response against human influenza vaccine with the simple submicron oil/water emulsion adjuvant MF59," Vaccine. 13(16):1557-62.
Palache et al. (1997). "Immunogenicity and reactogenicity of influenza subunit vaccines produced in MDCK cells or fertilized chicken eggs," J Infect Dis, 176 Suppl 1:S20-3.
Petrovsky et al. (2004). "Vaccine adjuvants: current state and future trends," Immunol Cell Biol. 82(5):488-96.
Wong et al. (2005). "Influenza vaccination: options and issues," Hong Kong Med J.11 (5):381-90.
Frey et al. (Vaccine 2003 vol. 21, pp. 4234-4237).
Palker et al. (Virus Research, Oct. 2004, vol. 105, No. 2, pp. 183-194).
O'Hagan et al. (2004). "Novel approaches to vaccine delivery," Pharma Res 21 (9):1519-1530.
Plotnicky et al. (2003). "The immunodominant influenza matrix T cell epitope recognized in human induces influenza protection in HLA-A2/$K^b$ transgenic mice," Virol 309:320-329.
Podda and Del Giudice (2003). "MF59-adjuvanted vaccines: increased immunogenicity with an optimal safety profile," Exp Rev Vaccine 2(2):197-204.
Singh et al. (2005). "A preliminary evaluation of alternative adjuvants to alum using a range of established and new generation vaccine antigens," Vaccine 24(10):1680-1686.
Wack et al. (2008). "Combination adjuvants for the induction of potent, long-lasting antibody and T-cell responses to influenza in mice," Vaccine 26:552-561.
Yasuda et al. (2010). "Comparison of half and full doses of an MF59-adjuvanted cell culture-derived A/H1N1 v vaccine in Japanese children," Adv Ther 27(7):444-457.
No Author, FLUAD® Product Monograph, No. ATC: J07BB02, Novartis Vaccines and Diagnostics, Inc., Cambridge, MA, May 8, 2013, pp. 1-27.
ChemBlink as www.chemolink.com. page 1, 2010.
Klang et al., International Journal of Pharmaceutics 1996, vol. 132, pp. 33-44.
Anonymous, "Entscheidende Daten der Phase-III-Studie zeigen: Der mittels Zellkultur hergestellte Grippeimpfstoff von Novartis ist gut vertraglich und wirksam," Retrieved from http://www.klinikundforschung.de/news/061120_influenza.htm, Oct. 19, 2006.
Bruhl et al., "Humoral and self-mediated immunity to Viro cell-derived influenza vaccine," Vaccine, vol. 19, pp. 1149-1158, 2001.
Cooper et al., "Safety and immunogenicity of CPG 7909 injection as an adjuvant to Flurix influenza vaccine," Vaccine, vol. 22, Nos. 22-23, pp. 3136-3143, Aug. 2004.
Daems et al., "Anticipating crisis: Towards a pandemic flu vaccination strategy through alignment of public health and industrial policy," Vaccine, vol. 23, No. 50, pp. 5732-5742, Oct. 2005.
Frey et al., "Comparison of the safety, tolerability, and immunogenicity of a MF59-adjuvanted influenza vaccine on a non-adjuvanted in non-elderly adults," Vaccines, vol. 21, pp. 4234-4237, 2003.
Fukuda et al., "Inactivated Influenza Vaccines," in Vaccines, Plotkin & Orenstein, eds., Chapters 17 and 18, 2004, pp. 339-388.
Halperin et al., "Safety and immunogenicity of a trivalent, inactivated, mammalian cell I culture-derived influenza vaccine in healthy adults, seniors, and children," Vaccine, vol. 20, Nos. 7-8, pp. 1240-1247, Jan. 2002.
Hehme et al., "Immunogenicity of a monovalent, aluminum-adjuvanted influenza whole virus vaccine for pandemic use," Virus Res., vol. 103, Nos. 1-2, pp. 163-171, 2004.
International Search Report dated Apr. 3, 2007 for WO 2007/052055.
Joseph et al., "Liposomal immunostimulatory DNA sequence (ISS-ODN)," Vaccine, vol. 20, Nos. 27-28, pp. 3342-3354, Sep. 2002.
Marsland et al., "Allergic airway inflammation is exacerbated during acute influenza infection and correlates with increased allergen presentation and recruitment of allergen-specific T-helper type 2 cells," Clin. Exp. Allergy, vol. 34, pp. 1299-1306, 2004.
Nyerges et al., "Sensitizing activity to egg protein of an $AIPO_4$-adjuvated full virus influenza vaccine," Acta. Microbiol. Acad. Sci. Hung., vol. 29, pp. 245-253, 1982.

(56) References Cited

OTHER PUBLICATIONS

O'Hagan et al., "Synergistic adjuvant activity of immunostimulatory DNA and oil/water emulsions for immunization with HIV p55 gag antigen," Vaccine, vol. 20, 27-28, pp. 3389-3398, Sep. 2002.

Stephenson et al., "Boosting immunity to influenza H5N1 with M59-adjuvanted H5N3 A/Duck/Singapore/97 vaccine in a primed human population," Vaccine, vol. 21, No. 15, pp. 1687-1693, Apr. 2003.

Pickering et al., "Influenza virus pyrogenicity: central role of structural orientation of virion components and involvement of viral lipid and glycoproteins," J. Gen. Virol., vol. 73, pp. 1345-1354, 1992.

Pien, "Statement presented to committee on aging United States Senate," Internet article, URL: http://aging.senate.gov/_files/hrl33hp.pdf, pp. 1-15, Sep. 2004.

Weeke-Luttmann et al., "Anti-ovalbumin sensitizing ability in influenza vaccines in guinea pigs," Dev. Biol. Stand., vol. 39, pp. 219-222, 1977.

\* cited by examiner

ADJUVANTED VACCINES WITH NON-VIRION ANTIGENS PREPARED FROM INFLUENZA VIRUSES GROWN IN CELL CULTURE

CROSS-REFERENCE TO RELATED APPLICATIONS

This application is a continuation of U.S. patent application Ser. No. 12/092,325, filed Sep. 26, 2008, which is the U.S. national stage entry under 35 U.S.C. § 371 of International Patent Application No. PCT/GB2006/004128, filed Nov. 6, 2006, which claims benefit of priority to U.S. Provisional Patent Application No. 60/735,658, filed Nov. 11, 2005, and U.S. Provisional Patent Application No. 60/734,026, filed Nov. 4, 2005, all of which are incorporated herein by reference in their entirety.

All documents cited herein are incorporated by reference in their entirety.

TECHNICAL FIELD

This invention is in the field of adjuvanted vaccines for protecting against influenza virus infection.

BACKGROUND ART

The current standard method for influenza virus growth in vaccine manufacture uses embryonated SPF hen eggs, with virus being purified from the egg contents (allantoic fluid). More recently, however, viruses have been grown in cell culture, and this method has the potential for producing larger quantities of antigen in a shorter time. In addition, it offers the ability to produce viruses which, due to their avian pathogenicity, cannot be grown in eggs.

Reference 1, from scientists at Baxter, reports a comparison of trivalent whole-virion vaccines (WVV) prepared from viruses grown either on eggs or on Vero cells. The two vaccines were compared for their ability to induce humoral and cell-mediated immunity. The authors reported that the immunogenicity of the Vero-derived vaccine was comparable to that of the egg-derived vaccine, but that the Vero-derived vaccine was superior in terms of T cell responses. T cell responses are reported to be more resistant than antibody responses to seasonal influenza virus antigenic drift, thereby improving year-to-year immunity.

With these encouraging results, Baxter continued to develop the Vero-derived product, under the trade name PREFLUCEL™. In December 2004, however, Baxter suspended its Phase II/III clinical study because the rate of fever and associated symptoms was higher than seen with existing vaccines.

Thus there remains a need for a safe and effective vaccine based on influenza virus grown in cell culture rather than in eggs.

DISCLOSURE OF THE INVENTION

Various forms of influenza virus vaccine are currently available (e.g. see chapters 17 & 18 of reference 2). Many vaccines are based on live virus or inactivated virus, with inactivated vaccines being based on whole virions, 'split' virions, or on purified surface antigens (including hemagglutinin and neuraminidase). The failed PREFLUCEL™ product used whole influenza virions.

The use of whole virions may be associated with increased reactogenicity [3]. To avoid the reactogenic problems seen with the PREFLUCEL™ product, the invention does not use a whole virion antigen i.e. it uses a non-virion antigen (e.g. a split virion, or purified surface antigens). The antigens are derived from virus grown in cell culture. While T cell responses were reported [1] to be enhanced when using whole virions grown in cell culture, however, the data herein show only modest T cell responses when using non-virion antigens. To provide enhanced T cell responses, therefore, the invention combines the non-virion antigens with an adjuvant.

The PREFLUCEL™ product did not include an adjuvant, and adding adjuvants to influenza vaccines has previously been linked to potential hypersensitivity. For example, reference 4 reports that an alum-adjuvanted influenza vaccine could sensitize guinea pigs, while unadjuvanted vaccine did not, and that the anaphylactogenic activity of egg proteins was significantly increased by the adjuvant. Similarly, reference 5 reported that adsorption of influenza virus antigen to aluminum salts led to earlier ovalbumin sensitization compared to unadjuvanted antigen. Furthermore, reference 6 reports that animals who previously received alum-adjuvanted ovalbumin showed an exacerbated allergic response during the early stages of an influenza virus infection. Hypersensitivity to vaccine components is a particular problem for influenza vaccines, as they are usually administered every year. By avoiding an egg-based system for viral growth, the invention also advantageously avoids any ovalbumin-linked concerns, which could become more apparent as influenza vaccination becomes more widespread (e.g. as immunization is extended to patient groups who have not previously been indicated for vaccination, and as the proportion of patients who are immunized in indicated target groups increases).

Thus the invention provides an immunogenic composition comprising: (i) a non-virion influenza virus antigen, prepared from a virus grown in cell culture; and (ii) an adjuvant.

The invention also provides a method for preparing an immunogenic composition comprising the steps of combining: (i) a non-virion influenza virus antigen prepared from a virus grown in cell culture; and (ii) an adjuvant.

The invention also provides a kit comprising: (i) a first kit component comprising a non-virion influenza virus antigen prepared from a virus grown in cell culture; and (ii) a second kit component comprising an adjuvant.

The influenza virus antigen typically comprises an influenza virus haemagglutinin. The adjuvant is preferably an oil-in-water emulsion adjuvant, such as MF59, and more preferably does not include any aluminum salt(s). Oil-in-water emulsions have been found to enhance influenza-specific T cell responses, and they can also enhance memory B cell responses. In addition, they can improve cross-reactivity against heterovariant influenza strains, such that a vaccine may induce protective immunity even if the vaccine strain does not match the circulating strain.

The use of adjuvants with influenza vaccines has been described before. In references 7 & 8, aluminum hydroxide was used to adjuvant Vero-derived whole virion vaccines. In reference 9, a mixture of aluminum hydroxide and aluminum phosphate was used to adjuvant egg-derived vaccines, with the preferred vaccines being egg-produced monovalent vaccines against pandemic strains. In reference 57, aluminum hydroxide was used to adjuvant MDCK-derived inactivated virions. Reference 10, for instance in example 7, suggests using adjuvants with inactivated whole equine influenza viruses. Reference 11 discloses, for instance in example 5, using aluminum hydroxide with inactivated virus grown on chicken embryo cells. In example 2 of reference 12, various different adjuvants were used with a trivalent egg-derived split vaccine. In reference 13, aluminum salts were used to adjuvant monovalent egg-derived whole virion vaccines. In most of these prior art cases, however, adjuvant was used with a whole-virion vaccine, and was not used with an antigen derived from virus grown in cell culture. Moreover, adjuvants were used in an attempt to reduce the per-dose amount of antigen required, thereby permitting an increased number of doses in a pandemic situation, rather than to enhance the T cell responses of the vaccines.

The Influenza Virus Antigen

Compositions of the invention include an antigen which is prepared from influenza virions obtained after viral growth in a cell line. The antigen is a non-virion antigen, and will typically comprise haemagglutinin. Thus the invention does not encompass vaccines that use a live virus or a whole virion inactivated virus. Instead, the antigens invention are non-virion antigens, such as split virions, or purified surface antigens (including hemagglutinin and, usually, also including neuraminidase).

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses are well known in the art e.g. see refs. 14-19, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Influenza antigens can also be presented in the form of virosomes [20] (nucleic acid free viral-like liposomal particles), as in the INFLEXAL V™ and INVAVAC™ products, but it is preferred not to use virosomes with the present invention. Thus, in some embodiments, the influenza antigen is not in the form of a virosome.

The influenza virus may be attenuated. The influenza virus may be temperature-sensitive. The influenza virus may be cold-adapted. These three features are particularly useful when using live virus as an antigen.

Influenza virus strains for use in vaccines change from season to season. In the current inter-pandemic period, vaccines typically include two influenza A strains (H1N1 and H3N2) and one influenza B strain, and trivalent vaccines are typical. The invention may also use viruses from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may protect against one or more of influenza A virus hemagglutinin subtypes H1, H2, H3, H4, H5, H6, H7, H8, H9, H10, H11, H12, H13, H14, H15 or H16. The invention may protect against one or more of influenza A virus NA subtypes N1, N2, N3, N4, N5, N6, N7, N8 or N9.

As well as being suitable for immunizing against inter-pandemic strains, the adjuvanted compositions of the invention are particularly useful for immunizing against pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A virus with H5 haemagglutinin type is preferred for immunising against pandemic influenza, such as a H5N1 strain. Other possible strains include H5N3, H9N2, H2N2, H7N1 and H7N7, and any other emerging potentially pandemic strains. Within the H5 subtype, a virus may fall into HA clade 1, HA clade 1', HA clade 2 or HA clade 3 [21], with clades 1 and 3 being particularly relevant.

Other strains that can usefully be included in the compositions are strains which are resistant to antiviral therapy (e.g. resistant to oseltamivir [22] and/or zanamivir), including resistant pandemic strains [23].

Compositions of the invention may include antigen(s) from one or more (e.g. 1, 2, 3, 4 or more) influenza virus strains, including influenza A virus and/or influenza B virus. Monovalent vaccines are not preferred, and where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is preferred, including two influenza A virus strains and one influenza B virus strain.

In some embodiments of the invention, the compositions may include antigen from a single influenza A strain. In some embodiments, the compositions may include antigen from two influenza A strains, provided that these two strains are not H1N1 and H3N2. In some embodiments, the compositions may include antigen from more than two influenza A strains.

The influenza virus may be a reassortant strain, and may have been obtained by reverse genetics techniques. Reverse genetics techniques [e.g. 24-28] allow influenza viruses with desired genome segments to be prepared in vitro using plasmids. Typically, it involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred [29-31], and these methods will also involve the use of plasmids to express all or some (e.g. just the PB1, PB2, PA and NP proteins) of the viral proteins, with 12 plasmids being used in some methods.

To reduce the number of plasmids needed, a recent approach [32] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference 32 method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [33]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [34,35].

Thus the virus, particularly an influenza A virus, may include one or more RNA segments from a A/PR/8/34 virus (typically 6 segments from A/PR/8/34, with the HA and N segments being from a vaccine strain, i.e. a 6:2 reassortant). It may also include one or more RNA segments from a A/WSN/33 virus, or from any other virus strain useful for generating reassortant viruses for vaccine preparation. Typically, the invention protects against a strain that is capable of human-to-human transmission, and so the strain's genome will usually include at least one RNA segment that originated in a mammalian (e.g. in a human) influenza virus. It may include NS segment that originated in an avian influenza virus.

The viruses used as the source of the antigens are grown on cell culture. The cell substrate will typically be a mammalian cell line. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. The use of mammalian cells means that vaccines can be free from chicken DNA, as well as being free from egg proteins (such as ovalbumin and ovomucoid). Preferred mammalian cell lines for growing influenza viruses include: MDCK cells [36-39], derived from Madin Darby canine kidney; Vero cells [40-42], derived from African green monkey (*Cercopithecus aethiops*) kidney; or PER.C6 cells [43], derived from human embryonic retinoblasts. These cell lines are widely available e.g. from the American Type Cell Culture (ATCC) collection [44], from the Coriell Cell Repositories [45], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 46-48], including cell lines derived from ducks (e.g. duck retina) or hens e.g. chicken embryo fibroblasts (CEF), avian embryonic stem cells [46, 49], including the EBx cell line derived from chicken embryonic stem cells, EB45, EB14, and EB14-074 [50], etc.

The most preferred cell lines for growing influenza viruses are MDCK cell lines. The original MDCK cell line is available from the ATCC as CCL-34, but derivatives of this cell line may also be used. For instance, reference 36 discloses a MDCK cell line that was adapted for growth in suspension culture ('MDCK 33016', deposited as DSM ACC 2219). Similarly, reference 51 discloses a MDCK-derived cell line that grows in suspension in serum-free culture ('B-702', deposited as FERM BP-7449). Reference 52 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 53 discloses MDCK cell lines with high susceptibility to infection, including 'MDCK.5F1' cells (ATCC CRL-12042). Any of these MDCK cell lines can be used.

The cell culture used for growth, and also the viral inoculum used to start the culture, is preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [54]. Absence of herpes simplex viruses is particularly preferred.

Virus may be grown on cells in suspension [36,55,56] or in adherent culture. One suitable MDCK cell line for suspension culture is MDCK 33016 (deposited as DSM ACC 2219). As an alternative, microcarrier culture can be used.

The cell lines are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

The cell lines are preferably cultured for growth at below 37° C. [57] (e.g. 30-36° C., or at about 30° C., 31° C., 32° C., 33° C., 34° C., 35° C., 36° C.), for example during viral replication.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

Haemagglutinin (HA) is the main immunogen in inactivated influenza vaccines, and vaccine doses are standardised by reference to HA levels, typically as measured by a single radial immunodiffution (SRID) assay. Existing vaccines typically contain about 15 μg of HA per strain, although the inclusion of an adjuvant advantageously means that lower doses can be used. Fractional doses such as ½ (i.e. 7.5 μg HA per strain), ¼ and ⅛ have been used [9,13], as have higher doses (e.g. 3× or 9× doses [58,59]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 15, about 10, about 7.5, about 5, about 3.8, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

HA used with the invention may be a natural HA as found in a virus, or may have been modified. For instance, it is known to modify HA to remove determinants (e.g. hyperbasic regions around the cleavage site between HA1 and HA2) that cause a virus to be highly pathogenic in avian species.

Compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10 and polysorbate 80. Other residual components in trace amounts could be antibiotics (e.g. neomycin, kanamycin, polymyxin B).

Vaccines of the invention may include matrix protein, in order to benefit from the additional T cell epitopes that are located within this antigen. Thus a vaccine (particularly a split vaccine) that includes haemagglutinin and neuraminidase may additionally include M1 and/or M2 matrix protein. Where a matrix protein is present, inclusion of detectable levels of M2 matrix protein is preferred. Nucleoprotein may also be present.

As a less preferred alternative to preparing antigens from influenza virions obtained after viral growth in a cell line, non-virion antigens can in some embodiments of the invention be prepared by expression in a recombinant host. For example, haemagglutinin and/or neuraminidase can be expressed in a recombinant host (e.g. in an insect cell line using a baculovirus vector) [60,61].

Host Cell DNA

Where virus has been grown on a cell line then it is standard practice to minimize the amount of residual cell line DNA in the final vaccine, in order to minimize any oncogenic activity of the DNA.

Vaccines of the invention preferably contain less than 10 ng (preferably less than 1 ng, and more preferably less than 100pg) of residual host cell DNA per dose, although trace amounts of host cell DNA may be present. Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 62 & 63, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [64].

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 μg of haemagglutinin are more preferred, as are vaccines containing <10 ng (e.g. <1 ng, <100 pg) host cell DNA per 0.5 ml volume.

It is preferred that the average length of any residual host cell DNA is less than 500 bp e.g. less than 400 bp, less than 300 bp, less than 200 bp, less than 100 bp, etc.

Measurement of residual host cell DNA is now a routine regulatory requirement for biologicals and is within the normal capabilities of the skilled person. The assay used to measure DNA will typically be a validated assay [65,66]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots [67]; immunoassay methods, such as the Threshold™ System [68]; and quantitative PCR [69]. These methods are all familiar to the skilled person, although the precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals [68]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 70.

The Adjuvant

Compositions of the invention include an adjuvant, which can function to enhance the T cell responses elicited in a patient who receives the composition e.g. enhance the number of T cells in the patient that release cytokines specifically in response to stimulation by an influenza antigen.

References 7-13 disclose the use of aluminum salt adjuvants with influenza virus antigens. Although aluminum salts can be used with the invention, they are preferably avoided i.e. it is preferred that the adjuvant does not consist of one or more aluminum salts. Aluminum sensitization has been reported [71-77]. The most preferred adjuvants for use with the invention comprise oil-in-water emulsions, as described in more detail below. Other adjuvants that can be used include, but are not limited to:

Cytokine-inducing agents (see below).

A mineral-containing composition, including calcium salts and aluminum salts (or mixtures thereof). Calcium salts include calcium phosphate (e.g. the "CAP" particles disclosed in ref. 78). Aluminum salts (which are not preferred adjuvants for use with the invention) include hydroxides (e.g. oxyhydroxides), phosphates (e.g. hydroxyphosphates, orthophosphates), sulfates, etc. [e.g. see chapters 8 & 9 of ref. 79], with the salts taking any suitable form (e.g. gel, crystalline, amorphous, etc.). Adsorption to these salts is preferred. The mineral containing compositions may also be formulated as a particle of metal salt [80].

Saponins [chapter 22 of ref. 118], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 81. Saponin formulations may also comprise a sterol, such as cholesterol [82]. Combinations of saponins and cholesterols can be used to form unique particles called immunostimulating complexs (ISCOMs) [chapter 23 of ref. 118]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 82-84. Optionally, the ISCOMS may be devoid of additional detergent [85]. A review of the development of saponin based adjuvants can be found in refs. 86 & 87.

Derivatives of lipid A from *Escherichia coli* such as OM-174, which is described in refs. 88 & 89.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [90]. The use of detoxified ADP-ribosylating toxins as mucosal adjuvants is described in ref. 91 and as parenteral adjuvants in ref. 92.

Bioadhesives and mucoadhesives, such as esterified hyaluronic acid microspheres [93] or chitosan and its derivatives [94].

Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref. 118). Examples of liposome formulations suitable for use as adjuvants are described in refs. 95-97.

Polyoxyethylene ethers and polyoxyethylene esters [98]. Such formulations further include polyoxyethylene sorbitan ester surfactants in combination with an octoxynol [99] as well as polyoxyethylene alkyl ethers or ester surfactants in combination with at least one additional non-ionic surfactant such as an octoxynol [100]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Muramyl peptides, such as N-acetylmuramyl-L-threonyl-D-isoglutamine ("thr-MDP"), N-acetyl-normuramyl-L-alanyl-D-isoglutamine (nor-MDP), N-acetyl-glucsaminyl-N-acetylmuramyl-L-Al-D-isoglu-L-Ala-dipalmitoxy propylamide ("DTP-DPP", or "Theramide™), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

An outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines [101].

Methyl inosine 5'-monophosphate ("MIMP") [102].
A polyhydroxlated pyrrolizidine compound [103], such as one having formula:

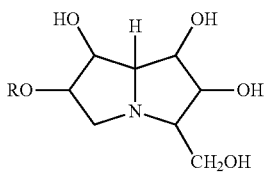

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A gamma inulin [104] or derivative thereof, such as algammulin.

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred [105].

A CD1d ligand, such as an α-glycosylceramide [106-113] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

etc.

These and other adjuvant-active substances are discussed in more detail in references 118 & 119.

Compositions may include two or more of said adjuvants. For example, they may advantageously include both an oil-in-water emulsion and a cytokine-inducing agent, as this combination improves the cytokine responses elicited by influenza vaccines, such as the interferon-γ response, with the improvement being much greater than seen when either the emulsion or the agent is used on its own.

Oil-in-Water Emulsion Adjuvants

Oil-in-water emulsions have been found to be particularly suitable for use in adjuvanting influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

The MF59 oil-in-water emulsion has been described for use as an adjuvant for egg-derived influenza vaccines [114], as in the FLUAD™ product, but the vaccines of the invention can be used more widely in the general population than the FLUAD™ product as they avoid the risk of sensitization to egg proteins, such as ovalbumin and ovomucoid.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Nonionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [115-117], as described in more detail in Chapter 10 of ref. 118 and chapter 12 of ref. 119. The MF59 emulsion advantageously includes citrate ions e.g. 10 mM sodium citrate buffer.
- An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100). The emulsion may also include a 3d-MPL. The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL. The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [120] (0.05-1% Thr-MDP, 5% squalane, 2.5% Pluronic L121 and 0.2% polysorbate 80). It can also be used without the Thr-MDP, as in the "AF" adjuvant [121] (5% squalane, 1.25% Pluronic L121 and 0.2% polysorbate 80). Microfluidisation is preferred.
- An emulsion having from 0.5-50% of an oil, 0.1-10% of a phospholipid, and 0.05-5% of a non-ionic surfactant. As described in reference 122, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 123, produced by addition of aliphatic amine to desacylsaponin via the carboxyl group of glucuronic acid), dimethyidioctadecylammonium bromide and/or N,N-dioctadecyl-N, N-bis (2-hydroxyethyl)propanediamine.
- An emulsion in which a saponin (e.g. QuilA or QS21) and a sterol (e.g. a cholesterol) are associated as helical micelles [124].
- An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [125].
- An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [125].

The emulsions are preferably mixed with antigen extemporaneously, at the time of delivery. Thus the adjuvant and antigen are typically kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

After the antigen and adjuvant have been mixed, haemagglutinin antigen will generally remain in aqueous solution but may distribute itself around the oil/water interface. In general, little if any haemagglutinin will enter the oil phase of the emulsion.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group [126] and a significant impact on the expression of genes involved in the Th1/Th2 balance [127]. They also have antioxidant properties that may help to stabilize the emulsions [128]. A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds [17].

Cytokine-Inducing Agents

Cytokine-inducing agents for inclusion in compositions of the invention are able, when administered to a patient, to elicit the immune system to release cytokines, including interferons and interleukins. Cytokine responses are known to be involved in the early and decisive stages of host defense against influenza infection [129]. Preferred agents can elicit the release of one or more of: interferon-γ; interleukin-1; interleukin-2; interleukin-12; TNF-α; TNF-β; and GM-CSF. Preferred agents elicit the release of cytokines associated with a Th1-type immune response e.g. interferon-γ, TNF-α, interleukin-2. Stimulation of both interferon-γ and interleukin-2 is preferred. Egg-derived influenza vaccines have been reported to elicit higher interferon α and β responses than MDCK- or Vero-derived influenza vaccines [130].

As a result of receiving a composition of the invention, therefore, a patient will have T cells that, when stimulated with an influenza antigen, will release the desired cytokine(s) in an antigen-specific manner. For example, T cells purified form their blood will release γ-interferon when exposed in vitro to influenza virus haemagglutinin. Methods for measuring such responses in peripheral blood mononuclear cells (PBMC) are known in the art, and include ELISA, ELISPOT, flow-cytometry and real-time PCR. For example, reference 131 reports a study in which antigen-specific T cell-mediated immune responses against tetanus toxoid, specifically γ-interferon responses, were monitored, and found that ELISPOT was the most sensitive method to discriminate antigen-specific TT-induced responses from spontaneous responses, but that intracytoplasmic cytokine detection by flow cytometry was the most efficient method to detect re-stimulating effects.

Suitable cytokine-inducing agents include, but are not limited to:
- An immunostimulatory oligonucleotide, such as one containing a CpG motif (a dinucleotide sequence containing an unmethylated cytosine linked by a phosphate bond to a guanosine), or a double-stranded RNA, or an oligonucleotide containing a palindromic sequence, or an oligonucleotide containing a poly(dG) sequence.
- 3-O-deacylated monophosphoryl lipid A ('3dMPL', also known as 'MPL™') [132-135].
- An imidazoquinoline compound, such as Imiquimod ("R-837") [136,137], Resiquimod ("R-848") [138], and their analogs; and salts thereof (e.g. the hydrochloride salts). Further details about immunostimulatory imidazoquinolines can be found in references 139 to 143.
- A thiosemicarbazone compound, such as those disclosed in reference 144. Methods of formulating, manufacturing, and screening for active compounds are also described in reference 144. The thiosemicarbazones are particularly effective in the stimulation of human peripheral blood mononuclear cells for the production of cytokines, such as TNF-α.
- A tryptanthrin compound, such as those disclosed in reference 145. Methods of formulating, manufacturing, and screening for active compounds are also described in reference 145. The thiosemicarbazones are particularly effective in the stimulation of human peripheral blood mononuclear cells for the production of cytokines, such as TNF-α.
- A nucleoside analog, such as: (a) Isatorabine (ANA-245; 7-thia-8-oxoguanosine):

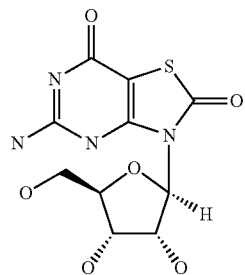 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 146 to 148; (1) a compound having the formula:

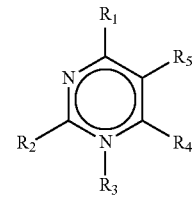

wherein:
$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;
$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;
$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

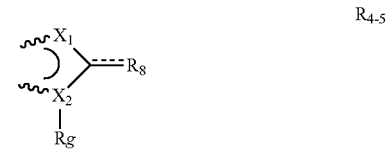

the binding being achieved at the bonds indicated by a ⌇
$X_1$ and $X_2$ are each independently N, C, O, or S;
$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—($C_{1-6}$ alkyl), —$S(O)_pR_e$, or —C(O)—$R_d$;
$R_9$ is H, $C_{1-6}$ alkyl, substituted $C_{1-6}$ alkyl, heterocyclyl, substituted heterocyclyl or $R_{9a}$, wherein $R_{9a}$ is:

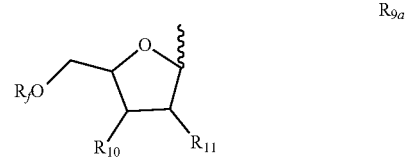

the binding being achieved at the bond indicated by a ⌇
$R_{10}$ and $R_{11}$ are each independently H, halo, $C_{1-6}$ alkoxy, substituted $C_{1-6}$ alkoxy, —$NR_aR_b$, or —OH;
each $R_a$ and $R_b$ is independently H, $C_{1-6}$ alkyl, substituted $C_{1-6}$ alkyl, —C(O)$R_d$, $C_{6-10}$ aryl;
each $R_c$ is independently H, phosphate, diphosphate, triphosphate, $C_{1-6}$ alkyl, or substituted $C_{1-6}$ alkyl;
each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —$NH(C_{1-6}$ alkyl), —NH(substituted $C_{1-6}$ alkyl), —$N(C_{1-6}$ alkyl)$_2$, —N(substituted $C_{1-6}$ alkyl)$_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —C(O)$R_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

Loxoribine (7-allyl-8-oxoguanosine) [149].

Compounds disclosed in reference 150, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [151,152], Hydrapthalamide compounds, Benzophenone compounds, Isoxazole compounds, Sterol compounds, Quinazilinone compounds, Pyrrole compounds [153], Anthraquinone compounds, Quinoxaline compounds, Triazine compounds, Pyrazalopyrimidine compounds, and Benzazole compounds [154].

A polyoxidonium polymer [155,156] or other N-oxidized polyethylene-piperazine derivative.

Compounds disclosed in reference 157.

A compound of formula I, II or III, or a salt thereof:

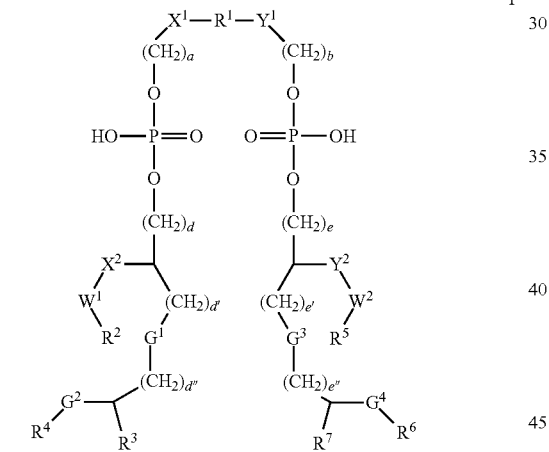

I

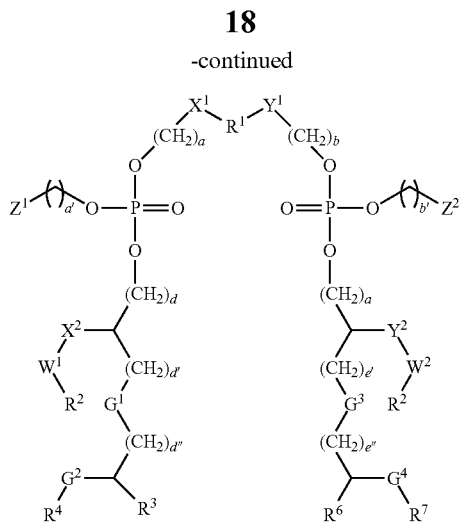

II

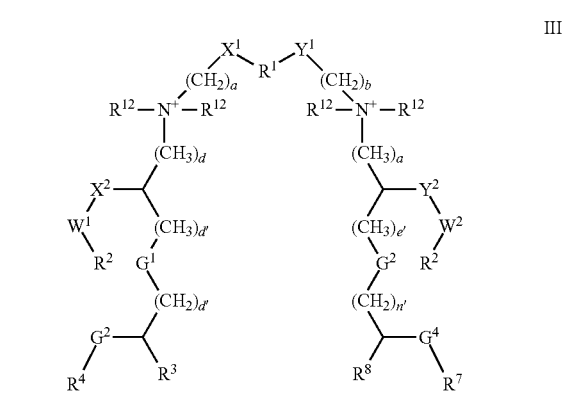

III as defined in reference 158, such as 'ER 803058', 'ER 803732', 'ER 804053', ER 804058', 'ER 804059', 'ER 804442', 'ER 804680', 'ER 804764', ER 803022 or 'ER 804057' e.g.:

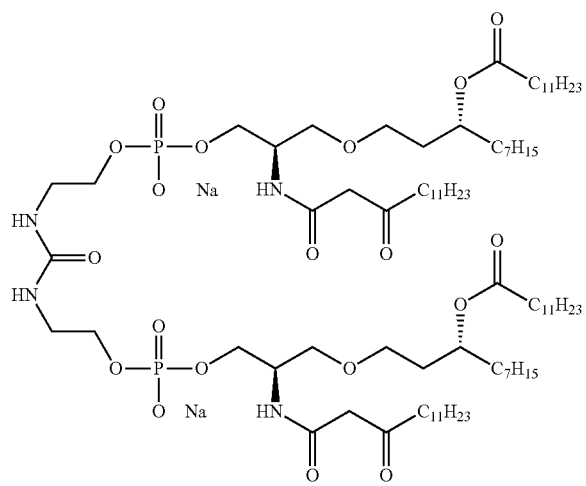

ER804057

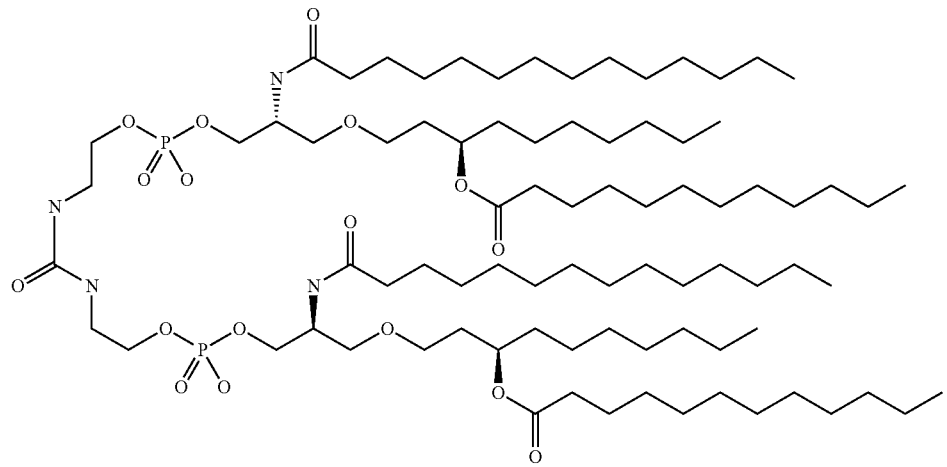

An aminoalkyl glucosaminide phosphate derivative, such as RC-529 [159,160].

A phosphazene, such as poly[di(carboxylatophenoxy) phosphazene] ("PCPP") as described, for example, in references 161 and 162.

Compounds containing lipids linked to a phosphate-containing acyclic backbone, such as the TLR4 antagonist E5564 [163,164]:

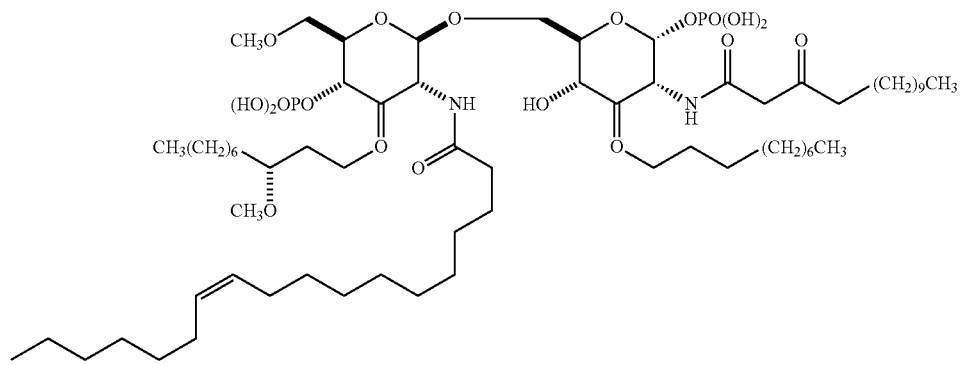

Small molecule immunopotentiators (SMIPs) such as:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo[4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propylamino)-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;

N4,N4-dibenzyl-1-(2-methoxy-2-methylpropyl)-N2-propyl-1H-imidazo[4,5-c]quinoline-2,4-diamine.

The cytokine-inducing agents for use in the present invention may be modulators and/or agonists of Toll-Like Receptors (TLR). For example, they may be agonists of one or more of the human TLR1, TLR2, TLR3, TLR4, TLR7, TLR8, and/or TLR9 proteins. Preferred agents are agonists of TLR7 (e.g. imidazoquinolines) and/or TLR9 (e.g. CpG oligonucleotides). These agents are useful for activating innate immunity pathways.

The cytokine-inducing agent can be added to the composition at various stages during its production. For example, it may be within an antigen composition, and this mixture can then be added to an oil-in-water emulsion. As an alternative, it may be within an oil-in-water emulsion, in which case the agent can either be added to the emulsion components before emulsification, or it can be added to the emulsion after emulsification. Similarly, the agent may be coacervated within the emulsion droplets. The location and distribution of the cytokine-inducing agent within the final composition will depend on its hydrophilic/lipophilic properties e.g. the agent can be located in the aqueous phase, in the oil phase, and/or at the oil-water interface.

The cytokine-inducing agent can be conjugated to a separate agent, such as an antigen (e.g. CRM197). A general review of conjugation techniques for small molecules is provided in ref. 165. As an alternative, the adjuvants may be non-covalently associated with additional agents, such as by way of hydrophobic or ionic interactions.

Two preferred cytokine-inducing agents are (a) immunostimulatory oligonucleotides and (b) 3dMPL.

Immunostimulatory oligonucleotides can include nucleotide modifications/analogs such as phosphorothioate modifications and can be double-stranded or (except for RNA) single-stranded. References 166, 167 and 168 disclose possible analog substitutions e.g. replacement of guanosine with 2'-deoxy-7-deazaguanosine. The adjuvant effect of CpG oligonucleotides is further discussed in refs. 169-174. A CpG sequence may be directed to TLR9, such as the motif GTCGTT or TTCGTT [175]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 176-178. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 175 & 179-181. A useful CpG adjuvant is CpG7909, also known as ProMune™ (Coley Pharmaceutical Group, Inc.).

As an alternative, or in addition, to using CpG sequences, TpG sequences can be used[182]. These oligonucleotides may be free from unmethylated CpG motifs.

The immunostimulatory oligonucleotide may be pyrimidine-rich. For example, it may comprise more than one consecutive thymidine nucleotide (e.g. TTTT, as disclosed in ref. 182), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 182), and/or it may have a nucleotide composition with >25% cytosine (e.g. >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF (see also ref. 183). Preparation of 3dMPL was originally described in reference 184.

3dMPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position. The group attached to carbon 2 has formula —NH—CO—CH$_2$—CR$^1$R$^{1'}$. The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is:

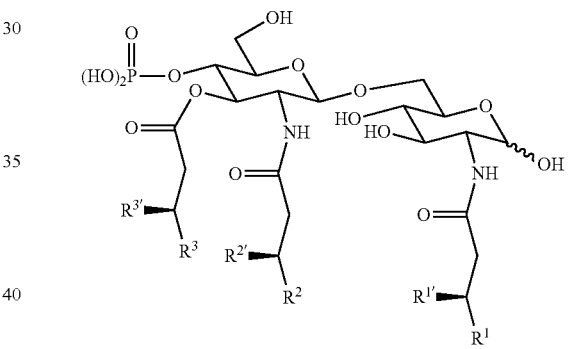

Groups R$^1$, R$^2$ and R$^3$ are each independently —(CH$_2$)$_n$—CH$_3$. The value of 72 is preferably between 8 and 16, more preferably between 9 and 12, and is most preferably 10.

Groups R$^{1'}$, R$^{2'}$ and R$^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, in is preferably 10. At the 3' position, m is preferably 12. Groups R$^{1'}$, R$^{2'}$ and R$^{3'}$ are thus preferably —O-acyl groups from dodecanoic acid, tetradecanoic acid or hexadecanoic acid.

When all of R$^{1'}$, R$^{2'}$ and R$^{3'}$ are —H then the 3dMPL has only 3 acyl chains (one on each of positions 2, 2' and 3'). When only two of R$^{1'}$, R$^{2'}$ and R$^{3'}$ are —H then the 3dMPL can have 4 acyl chains. When only one of R$^{1'}$, R$^{2'}$ and R$^{3'}$ is —H then the 3dMPL can have 5 acyl chains. When none of R$^{1'}$, R$^{2'}$ and R$^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g. ≥20%, ≥30%, ≥40%, ≥50% or more. 3dMPL with 6 acyl chains has been found to be the most adjuvant-active form.

Thus the most preferred form of 3dMPL for inclusion in compositions of the invention is:

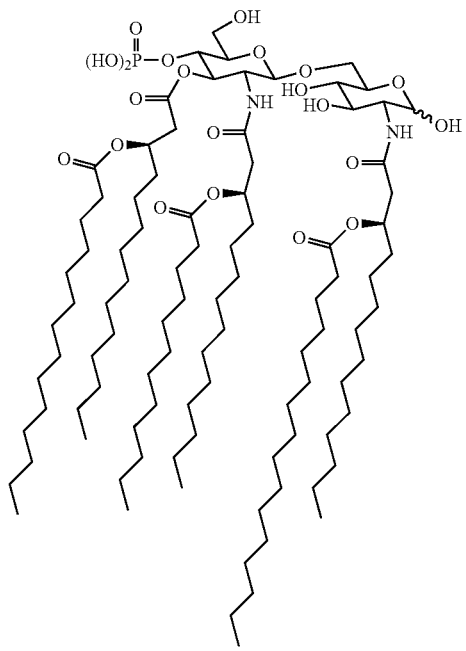

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [185]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g. ≥60%, ≥70%, ≥80%, ≥90%, or more) of the particles will have a diameter within the range x±25%.

3dMPL can advantageously be used in combination with an oil-in-water emulsion. Substantially all of the 3dMPL may be located in the aqueous phase of the emulsion.

A typical amount of 3dMPL in a vaccine is 10-100 µg/dose e.g. about 25 µg or about 50 µg.

The 3dMPL can be used on its own, or in combination with one or more further compounds. For example, it is known to use 3dMPL in combination with the QS21 saponin [186] (including in an oil-in-water emulsion [187]), with an immunostimulatory oligonucleotide, with both QS21 and an immunostimulatory oligonucleotide, with aluminum phosphate [188], with aluminum hydroxide [189], or with both aluminum phosphate and aluminum hydroxide.

Pharmaceutical Compositions

Compositions of the invention are pharmaceutically acceptable. They may include components in addition to the antigen and adjuvant e.g. they typically include one or more pharmaceutical carrier(s) and/or excipient(s). A thorough discussion of such components is available in reference 190.

Compositions will generally be in aqueous form. The antigen and adjuvant will typically be in admixture.

The composition may include preservatives such as thiomersal or 2-phenoxyethanol. It is preferred, however, that the vaccine should be substantially free from (i.e. less than 5 µg/ml) mercurial material e.g. thiomersal-free [17,191]. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [192], but keeping osmolality in this range is nevertheless preferred.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Kits of the Invention

Compositions of the invention may be prepared extemporaneously, at the time of delivery. Thus the invention provides kits including the various components ready for mixing. The kit allows the adjuvant and the antigen to be kept separately until the time of use. This arrangement is particularly useful when using an oil-in-water emulsion adjuvant.

The components are physically separate from each other within the kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container.

In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe, such as those disclosed in references 193-200 etc. When the syringe is actuated (e.g. during administration to a patient) then the contents of the two chambers are mixed. This arrangement avoids the need for a separate mixing step at the time of use.

The kit components will generally be in aqueous form. In some arrangements, a component (typically the antigen component rather than the adjuvant component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

Packaging of Compositions or Kit Components

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

Compositions of the invention are suitable for administration to human patients, and the invention provides a method of raising an immune response in a patient, comprising the step of administering a composition of the invention to the patient.

The invention also provides a kit or composition of the invention for use as a medicament.

The invention also provides the use of (i) a non-virion influenza virus antigen, prepared from a virus grown in cell culture; and (ii) an adjuvant, in the manufacture of a medicament for raising an immune response in a patient.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [201]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [202-204], oral [205], intradermal [206,207], transcutaneous, transdermal [208], etc.

Vaccines prepared according to the invention may be used to treat both children and adults. Influenza vaccines are currently recommended for use in pediatric and adult immunisation, from the age of 6 months. Thus the patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, immunodeficient patients, patients who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (≥60 years), these criteria are: (1) ≥60% seroprotection; (2) ≥30% seroconversion; and/or (3) a GMT increase of ≥2-fold. These criteria are based on open label studies with at least 50 patients.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonie acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

BRIEF DESCRIPTION OF DRAWINGS

FIG. 2 shows the H1N1 results; FIG. 3 shows H3N2; FIG. 4 shows influenza B.

Modes for Carrying Out the Invention

Figure 1:
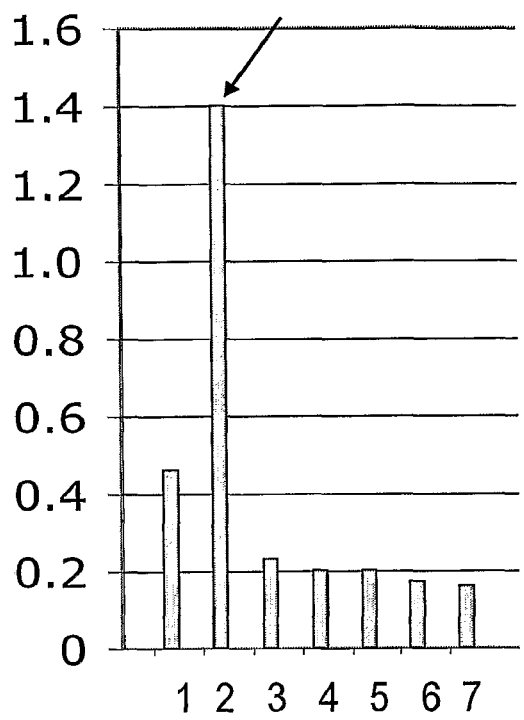
FIG. 1 shows the percentage of CD4$^+$ T cells that gave an antigen-specific cytokine response when stimulated by HA.

Influenza virus strains Wyoming H3N2 (A), New-Caledonia H1N1 (A) and Jiangsu (B) were separately grown on MDCK cells, thereby avoiding the presence of any egg-derived proteins (specifically ovalbumin) in the final vaccines. A trivalent surface glycoprotein vaccine was prepared and was used to immunize immune-naïve Balb/C mice at two doses (0.1 and 1 μg HA per strain) at days 0 and 28. Animals were bled at day 42 and various assays were performed with the blood: HI titers; anti-HA responses, measured by ELISA; and the level of CD4$^+$ T cells that release cytokines in an antigen-specific manner, including a separate measurement of those that release γ-interferon. IgG responses were measured specifically in respect of IgG1 and IgG2a.

In contrast to the reports in reference 1 of enhanced T cell responses when using antigens purified from influenza grown in mammalian cell culture, only a modest number of $CD4^+$ T cells released cytokines in an antigen-specific manner. To improve these results, vaccines were adjuvanted with one of the following: (1) an aluminum hydroxide, used at 1 mg/ml and including a 5 mM histidine buffer; (2) MF59 oil-in-water emulsion with citrate buffer mixed at a 1:1 volume ratio with the antigen solution; (3) calcium phosphate, used at 1 mg/ml and including a 5 mM histidine buffer; (4) microparticles formed from poly(lactide co-glycolide) 50:50 co-polymer composition, intrinsic viscosity 0.4 ('PLG'), with adsorbed antigen; (5) a CpG immunostimulatory oligonucleotide with a phosphorothioate backbone; (6) resiquimod; or (7) a negative control with no adjuvant.

FIG. 1 shows the number of T cells that release cytokine(s) in an antigen-specific manner after immunization with one of the seven compositions. Each of the six adjuvants increased the T cell responses, but the emulsion-based composition (arrow) gave by far the best enhancement.

Figure 2:
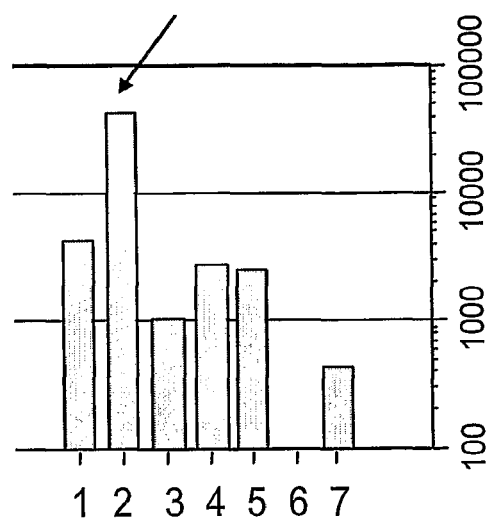
FIGS. 2 to 4 show the Log 10 serum antibody titers (ELISA) for mice immunized with different compositions. Arrows show compositions adjuvanted by the MF59 emulsion.
Figure 3:
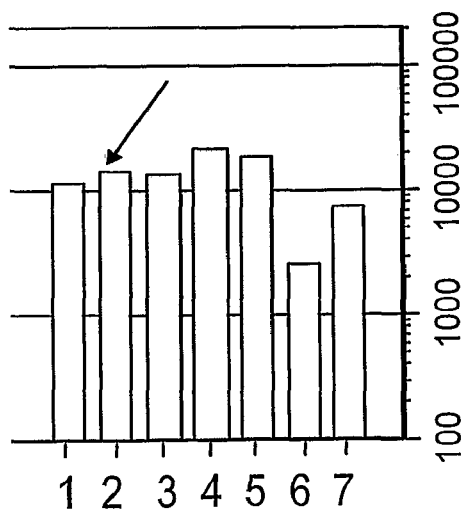
Figure 4:
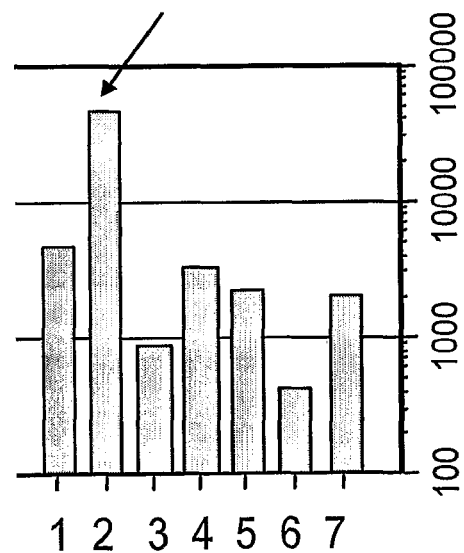
Figure 5:
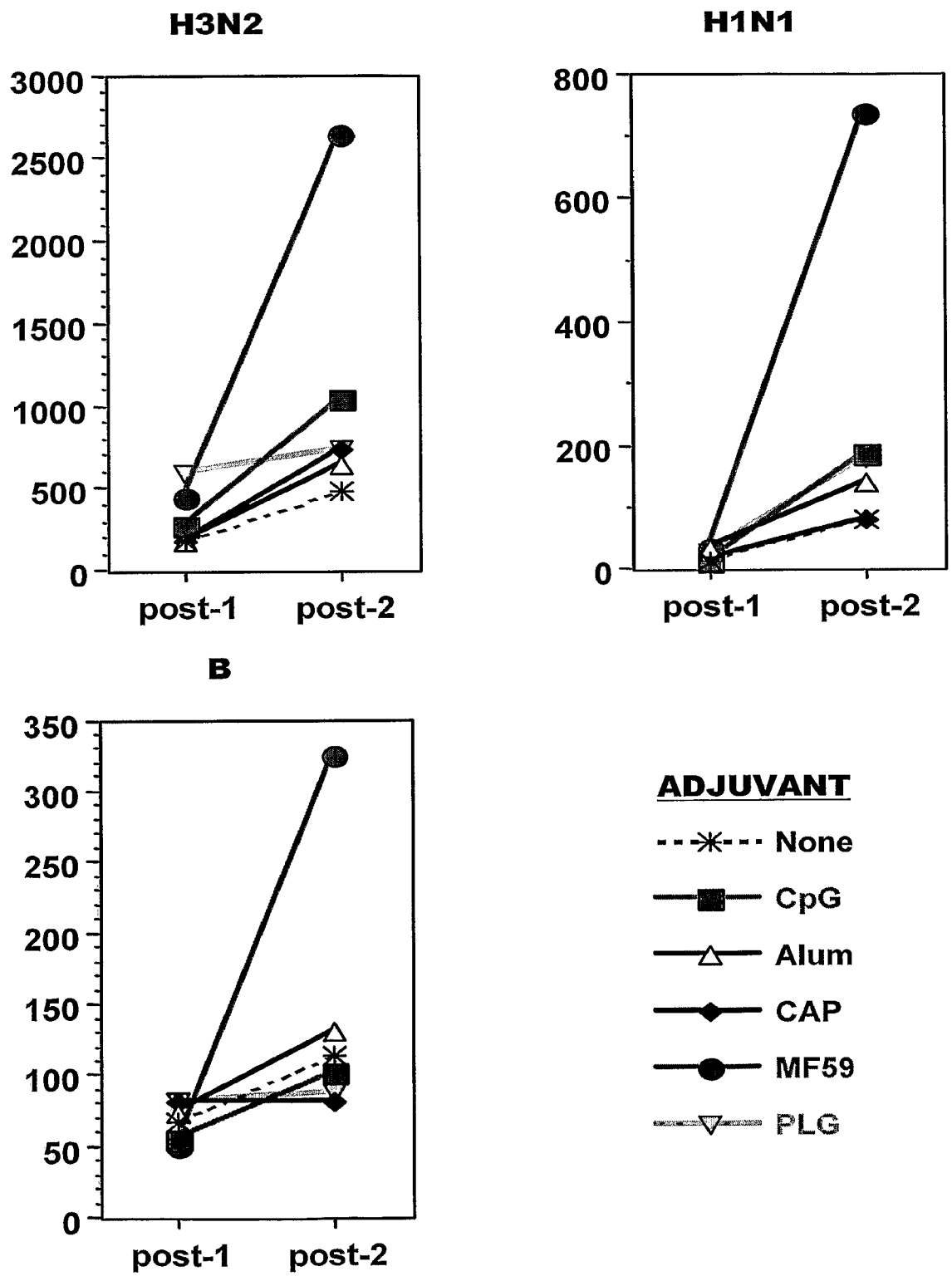
FIG. 5 shows serum HI titers with different adjuvants.

FIGS. 2 to 4 show anti-HA ELISA responses. From these Figures, and from similar data in FIG. 5, it is again apparent that the emulsion-based composition gave the best responses. The data in FIG. 5 also show a good anti-HA response when using an immunostimulatory oligonucleotide.

Figure 6:
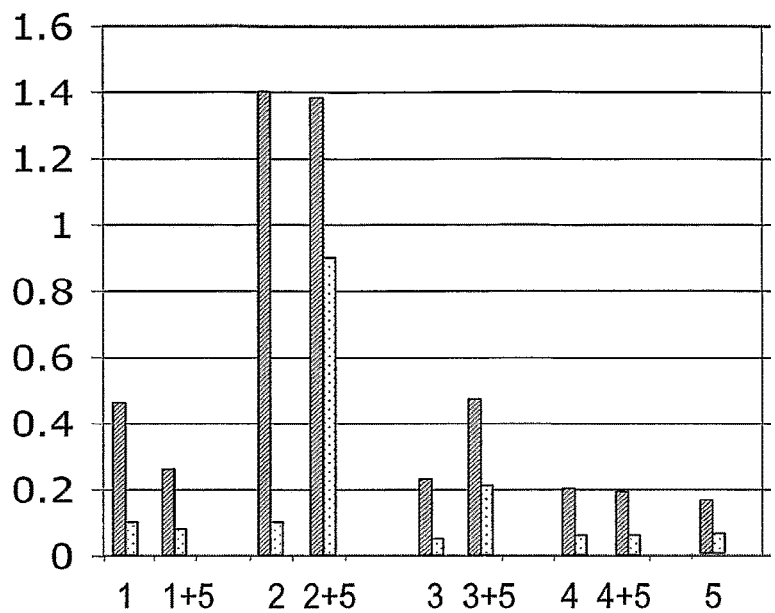
FIG. 6 is similar to FIG. 1, and shows the effect of adding CpG to various adjuvants. The left bar of each pair shows the % of cells with an antigen-specific cytokine response; the right bar shows the % of cells which show an antigen-specific interferon-γ response.

FIG. 6 shows the effect on T cells of adding the CpG oligonucleotide (5) to adjuvants (1) to (4). With the emulsion (2), there is little effect on the overall T cell response, but the proportion of interferon-γ secreting cells is much greater, indicating a more TH1-like response. A similar effect is seen when CpG is added to calcium phosphate (3), but with an increased overall T cell response. Adding CpG to the aluminum hydroxide adjuvant had no beneficial effect on T cell responses.

Figure 7:
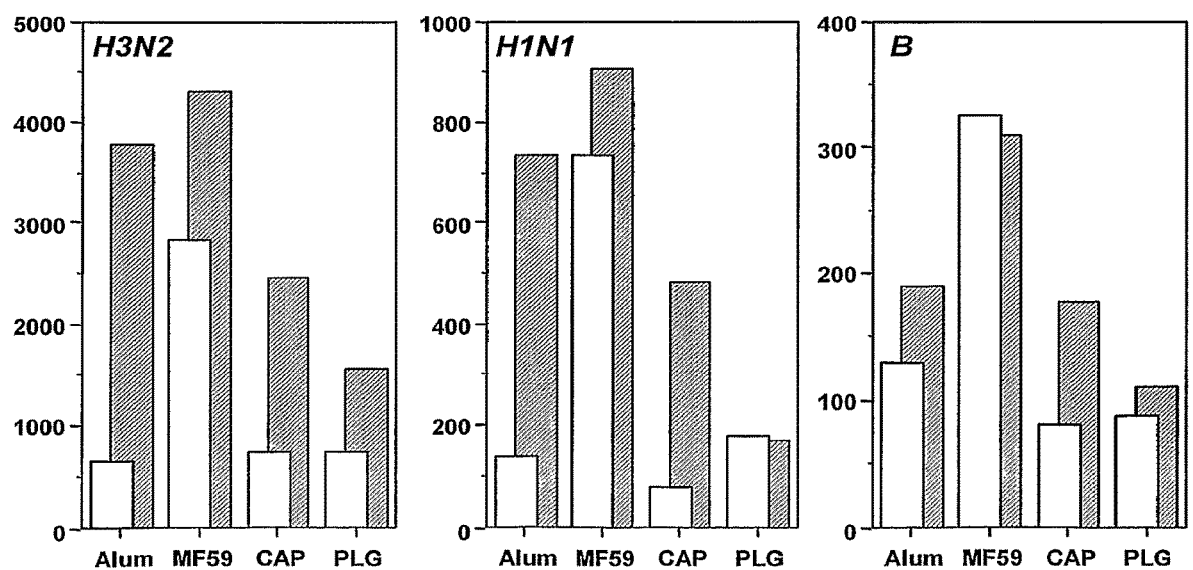
FIG. 7 is similar to FIG. 5, and shows HI titers for adjuvants (1) to (4), with (plain, foreground) and without (hatched, background) CpG when using 0.1 μg antigen.
Figure 8:
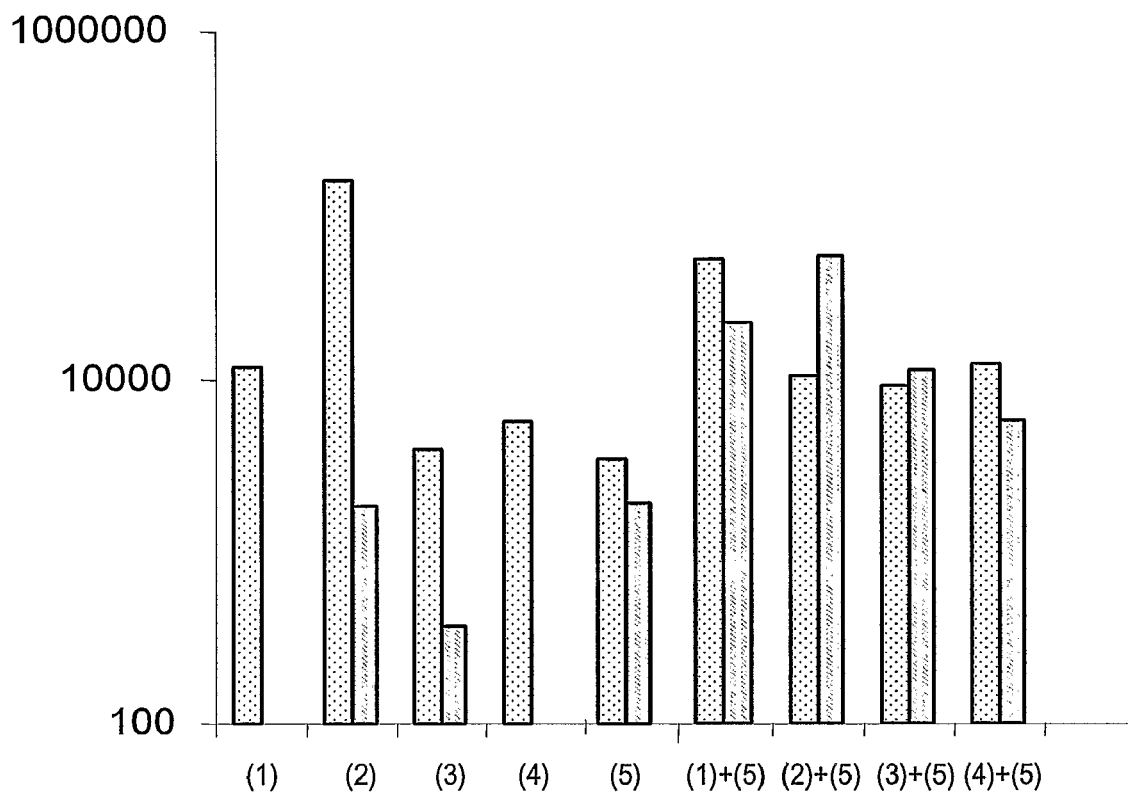
FIG. 8 shows GMTs (AU/ml) for IgG against the H3N2 strain with different adjuvants and combinations. The left bar in each pair shows IgG1; the right shows IgG2a. The scale is logarithmic.

The same shift towards a TH1-like response is seen in FIG. 8. Adjuvants (1) to (4) all showed a dominant IgG1 response (TH2) on their own, as did CpG (5) alone. Adding CpG to adjuvants (1) to (4) increased the levels of IgG2a (TH1) in all cases, including the production of an IgG2a response for the aluminum hydroxide and PLG adjuvants which was not seen in the absence of CpG. Moreover, the addition of CpG to the oil-in-water emulsion (2) and to calcium phosphate (3) shifted the IgG response such that IgG2a was dominant. Adding CpG to the adjuvants generally enhanced HI titers (FIG. 7). Thus addition of CpG enhances both T cell responses and B cell responses for all adjuvants, except for the aluminum salt.

Thus, in contrast to the findings in reference 1 using whole virion antigens derived from viruses grown in mammalian cell culture, antigen-specific T cell responses against purified influenza antigens were found to be weak in the absence of adjuvant. By adding adjuvants, however, T cell responses could be enhanced. In particular, oil-in-water emulsions are excellent adjuvants, both in terms of T cell responses and anti-HA antibodies. By both of these criteria the MF59 emulsion is superior to an aluminum salt adjuvant.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

[1] Brühl et al. (2001) *Vaccine* 19:1149-58.
[2] *Vaccines*. (eds. Plotkin & Orenstein). 4th edition, 2004, ISBN: 0-7216-9688-0.
[3] Pickering et al. (1992) *J Gen Virol* 73:1345-54.
[4] Nyerges et al. (1982) *Acta Microbiol Acad Sci Hung* 29:245-53.
[5] Weeke-Luttmann & Schramm-Thiel (1977) *Dev Biol Stand* 39:219-22.
[6] Marsland et al. (2004) *Clin Exp Allergy* 34:1299-306.
[7] U.S. Pat. No. 6,372,223.
[8] WO00/15251.
[9] WO01/22992.
[10] U.S. Pat. No. 4,500,513.
[11] WO96/15231.
[12] US 2004/0081686.
[13] Hehme et al. (2004) *Virus Res.* 103(1-2):163-71.
[14] WO02/28422.
[15] WO02/067983.
[16] WO2005/113756.
[17] WO02/097072.
[18] WO02/074336.
[19] WO01/21151.
[20] Huckriede et al. (2003) *Methods Enzymol* 373:74-91.
[21] World Health Organisation (2005) *Emerging Infectious Diseases* 11(10):1515-21.
[22] Herlocher et al. (2004) *J Infect Dis* 190(9):1627-30.
[23] Le et al. (2005) *Nature* 437(7062):1108.
[24] Hoffmann et al. (2002) *Vaccine* 20:3165-3170.
[25] Subbarao et al. (2003) *Virology* 305:192-200.
[26] Liu et al. (2003) *Virology* 314:580-590.
[27] Ozaki et al. (2004) *J Virol.* 78:1851-1857.
[28] Webby et al. (2004) *Lancet* 363:1099-1103.
[29] WO00/60050.
[30] WO01/04333.
[31] U.S. Pat. No. 6,649,372.
[32] Neumann et al. (2005) *Proc Natl Acad Sci USA* 102:16825-9.
[33] WO2006/067211.
[34] WO01/83794.
[35] Hoffmann et al. (2000) *Virology* 267(2):310-7.
[36] WO97/37000.
[37] Brands et al. (1999) *Dev Biol Stand* 98:93-100.
[38] Halperin et al. (2002) *Vaccine* 20:1240-7.
[39] Tree et al. (2001) *Vaccine* 19:3444-50.
[40] Kistner et al. (1998) *Vaccine* 16:960-8.
[41] Kistner et al. (1999) *Dev Biol Stand* 98:101-110.
[42] Bruhl et al. (2000) *Vaccine* 19:1149-58.
[43] Pau et al. (2001) *Vaccine* 19:2716-21.
[44] http://www.atcc.org/[45]
[45] http://locus.umdnj.edu/[46]
[46] WO03/076601.
[47] WO2005/042728.
[48] WO03/043415.
[49] WO01/85938.
[50] WO2006/108846.
[51] EP-A-1260581 (WO01/64846).
[52] WO2006/071563.
[53] WO2005/113758.
[54] WO2006/027698.
[55] WO03/023021.
[56] WO03/023025.
[57] WO97/37001.
[58] Treanor et al. (1996) *J Infect Dis* 173:1467-70.

[59] Keitel et al. (1996) *Clin Diagn Lab Immunol* 3:507-10.
[60] WO96/37624.
[61] WO98/46262.
[62] EP-B-0870508.
[63] U.S. Pat. No. 5,948,410.
[64] International patent application entitled "CELL-DERIVED VIRAL VACCINES WITH LOW LEVELS OF RESIDUAL CELL DNA", filed 1st November 2006 claiming priority U.S. 60/732,786.
[65] Lundblad (2001) *Biotechnology and Applied Biochemistry* 34:195-197.
[66] *Guidance for Industry: Bioanalytical Method Validation*. U.S. Department of Health and Human Services Food and Drug Administration Center for Drug Evaluation and Research (CDER) Center for Veterinary Medicine (CVM). May 2001.
[67] Ji et al. (2002) *Biotechniques.* 32:1162-7.
[68] Briggs (1991) *J Parenter Sci Technol.* 45:7-12.
[69] Lahijani et al. (1998) *Hum Gene Ther.* 9:1173-80.
[70] Lokteff et al. (2001) *Biologicals.* 29:123-32.
[71] Frederiksen & Tofte (2004) *Vaccine* 23(1):1-2.
[72] Bergfors et al. (2003) *Vaccine* 22(1):64-9.
[73] Skowron et al. (1998) *Contact Dermatitis* 39(3):135-6.
[74] Cosnes et al. (1990) *Contact Dermatitis* 23(2):65-7.
[75] Castelain et al. (1988) *Contact Dermatitis* 19(1):58-60.
[76] Veien et al. (1986) *Contact Dermatitis* 15(5):295-7.
[77] Bohler-Sommeregger & Lindemayr (1986) *Contact Dermatitis* 15(5):278-81.
[78] U.S. Pat. No. 6,355,271.
[79] *Vaccine Design* . . . (1995) eds. Powell & Newman. ISBN: 030644867X. Plenum.
[80] WO00/23105.
[81] U.S. Pat. No. 5,057,540.
[82] WO96/33739.
[83] EP-A-0109942.
[84] WO96/11711.
[85] WO00/07621.
[86] Barr et al. (1998) *Advanced Drug Delivery Reviews* 32:247-271.
[87] Sjolanderet et al. (1998) *Advanced Drug Delivery Reviews* 32:321-338.
[88] Meraldi et al. (2003) *Vaccine* 21:2485-2491.
[89] Pajak et al. (2003) *Vaccine* 21:836-842.
[90] Pizza et al. (2000) *Int J Med Microbiol* 290:455-461.
[91] WO95/17211.
[92] WO98/42375.
[93] Singh et al. (2001) *J Cont Release* 70:267-276.
[94] WO99/27960.
[95] U.S. Pat. No. 6,090,406
[96] U.S. Pat. No. 5,916,588
[97] EP-A-0626169.
[98] WO99/52549.
[99] WO01/21207.
[100] WO01/21152.
[101] WO02/072012.
[102] Signorelli & Hadden (2003) *Int Immunopharmacol* 3(8):1177-86.
[103] WO2004/064715.
[104] Cooper (1995) *Pharm Biotechnol* 6:559-80.
[105] U.S. Pat. No. 6,586,409.
[106] De Libero et al, *Nature Reviews Immunology*, 2005, 5: 485-496
[107] U.S. Pat. No. 5,936,076.
[108] Oki et al, *J. Clin. Investig.*, 113: 1631-1640
[109] US2005/0192248
[110] Yang et al, *Angew. Chem. Int. Ed.*, 2004, 43: 3818-3822
[111] WO2005/102049
[112] Goff et al, *J. Am. Chem., Soc.*, 2004, 126: 13602-13603
[113] WO03/105769
[114] Frey et al. (2003) *Vaccine* 21:4234-7.
[115] WO90/14837.
[116] Podda & Del Giudice (2003) *Expert Rev Vaccines* 2:197-203.
[117] Podda (2001) *Vaccine* 19: 2673-2680.
[118] *Vaccine Design: The Subunit and Adjuvant Approach* (eds. Powell & Newman) Plenum Press 1995 (ISBN 0-306-44867-X).
[119] *Vaccine Adjuvants: Preparation Methods and Research Protocols* (Volume 42 of *Methods in Molecular Medicine* series). ISBN: 1-59259-083-7. Ed. O'Hagan.
[120] Allison & Byars (1992) *Res Immunol* 143:519-25.
[121] Hariharan et al. (1995) *Cancer Res* 55:3486-9.
[122] WO95/11700.
[123] U.S. Pat. No. 6,080,725.
[124] WO2005/097181.
[125] WO2006/113373.
[126] Han et al. (2005) *Impact of Vitamin E on Immune Function and Infectious Diseases in the Aged at Nutrition, Immune functions and Health* EuroConference, Paris, 9-10 Jun. 2005.
[127] Han et al. (2004) *Ann NY Acad Sci* 1031:96-101.
[128] U.S. Pat. No. 6,630,161.
[129] Hayden et al. (1998) *J Clin Invest* 101(3):643-9.
[130] Miller & Anders (2003) *J Gen Virol* 84:193-202.
[131] Tassignon et al. (2005) *J Immunol Meth* 305:188-98.
[132] Myers et al. (1990) pages 145-156 of Cellular and molecular aspects of endotoxin reactions.
[133] Ulrich (2000) Chapter 16 (pages 273-282) of reference 119.
[134] Johnson et al. (1999) *J Med Chem* 42:4640-9.
[135] Baldrick et al. (2002) *Regulatory Toxicol Pharmacol* 35:398-413.
[136] U.S. Pat. No. 4,680,338.
[137] U.S. Pat. No. 4,988,815.
[138] WO92/15582.
[139] Stanley (2002) *Clin Exp Dermatol* 27:571-577.
[140] Wu et al. (2004) *Antiviral Res.* 64(2):79-83.
[141] Vasilakos et al. (2000) *Cell Immunol.* 204(1):64-74.
[142] U.S. Pat. Nos. 4,689,338, 4,929,624, 5,238,944, 5,266, 575, 5,268,376, 5,346,905, 5,352,784, 5,389,640, 5,395, 937, 5,482,936, 5,494,916, 5,525,612, 6,083,505, 6,440, 992, 6,627,640, 6,656,938, 6,660,735, 6,660,747, 6,664, 260, 6,664,264, 6,664,265, 6,667,312, 6,670,372, 6,677, 347, 6,677,348, 6,677,349, 6,683,088, 6,703,402, 6,743, 920, 6,800,624, 6,809,203, 6,888,000 and 6,924,293.
[143] Jones (2003) *Curr Opin Investig Drugs* 4:214-218.
[144] WO2004/060308.
[145] WO2004/064759.
[146] U.S. Pat. No. 6,924,271.
[147] US2005/0070556.
[148] U.S. Pat. No. 5,658,731.
[149] U.S. Pat. No. 5,011,828.
[150] WO2004/87153.
[151] U.S. Pat. No. 6,605,617.
[152] WO02/18383.
[153] WO2004/018455.
[154] WO03/082272.
[155] Dyakonova et al. (2004) *Int Immunopharmacol* 4(13): 1615-23.
[156] FR-2859633.
[157] WO2006/002422.
[158] WO03/011223.

[159] Johnson et al. (1999) *Bioorg Med Chem Lett* 9:2273-2278.
[160] Evans et al. (2003) *Expert Rev Vaccines* 2:219-229.
[161] Andrianov et al. (1998) *Biomaterials* 19:109-115.
[162] Payne et al. (1998) *Adv Drug Delivery Review* 31:185-196.
[163] Wong et al. (2003) *J Clin Pharmacol* 43(7):735-42.
[164] US2005/0215517.
[165] Thompson et al. (2003) *Methods in Molecular Medicine* 94:255-266.
[166] Kandimalla et al. (2003) *Nucleic Acids Research* 31:2393-2400.
[167] WO02/26757.
[168] WO99/62923.
[169] Krieg (2003) *Nature Medicine* 9:831-835.
[170] McCluskie et al. (2002) *FEMS Immunology and Medical Microbiology* 32:179-185.
[171] WO98/40100.
[172] U.S. Pat. No. 6,207,646.
[173] U.S. Pat. No. 6,239,116.
[174] U.S. Pat. No. 6,429,199.
[175] Kandimalla et al (2003) *Biochemical Society Transactions* 31 (part 3):654-658.
[176] Blackwell et al (2003) *J Immunol* 170:4061-4068.
[177] Krieg (2002) *Trends Immunol* 23:64-65.
[178] WO01/95935.
[179] Kandimalla et al. (2003) *BBRC* 306:948-953.
[180] Bhagat et al. (2003) *BBRC* 300:853-861.
[181] WO03/035836.
[182] WO01/22972.
[183] Thompson et al. (2005) *J Leukoc Biol* 78: The low-toxicity versions of LPS, MPL® adjuvant and RC529, are efficient adjuvants for CD4+ T cells'.
[184] UK patent application GB-A-2220211.
[185] WO 94/21292.
[186] WO94/00153.
[187] WO95/17210.
[188] WO96/26741.
[189] WO93/19780.
[190] Gennaro (2000) *Remington: The Science and Practice of Pharmacy*. 20th edition, ISBN: 0683306472.
[191] Banzhoff (2000) *Immunology Letters* 71:91-96.
[192] Nony et al. (2001) *Vaccine* 27:3645-51.
[193] WO2005/089837.
[194] U.S. Pat. No. 6,692,468.
[195] WO00/07647.
[196] WO99/17820.
[197] U.S. Pat. No. 5,971,953.
[198] U.S. Pat. No. 4,060,082.
[199] EP-A-0520618.
[200] WO98/01174.
[201] Potter & Oxford (1979) *Br Med Bull* 35: 69-75.
[202] Greenbaum et al. (2004) *Vaccine* 22:2566-77.
[203] Zurbriggen et al. (2003) *Expert Rev Vaccines* 2:295-304.
[204] Piascik (2003) *J Am Pharm Assoc* (Wash D.C.). 43:728-30.
[205] Mann et al. (2004) *Vaccine* 22:2425-9.
[206] Halperin et al. (1979) *Am J Public Health* 69:1247-50.
[207] Herbert et al. (1979) *J Infect Dis* 140:234-8.
[208] Chen et al. (2003) *Vaccine* 21:2830-6.

The invention claimed is:

1. A method of raising an immune response in a human comprising administering an effective amount of a composition to the human, wherein the composition comprises:
    (i) at least one non-virion influenza virus antigen, prepared from a cell culture-grown human influenza virus, and
    (ii) an adjuvant comprising an oil-in-water emulsion.
2. The method of claim 1, wherein the at least one non-virion influenza virus antigen comprises one or more purified surface antigens.
3. The method of claim 1, wherein the at least one non-virion influenza virus antigen comprises one or more split virions.
4. The method of claim 1, wherein the composition further comprises non-virion influenza virus antigens from more than one human influenza virus strain.
5. The method of claim 4, wherein the non-virion antigens are prepared from human influenza A virus and human influenza B virus.
6. The method of claim 1, wherein the at least one non-virion influenza virus antigen is from an H1, H2, H3, H5, H7, or H9 influenza A virus subtype.
7. The method of claim 1, wherein the composition contains from 0.1 to 20 µg of haemagglutinin per viral strain.
8. The method of claim 1, wherein the composition is free of chicken DNA, ovalbumin, and ovomucoid.
9. The method of claim 1, wherein the composition contains less than 10 ng of cellular DNA from cell culture host.
10. The method of claim 1, wherein the oil-in-water emulsion has sub-micron droplets.
11. The method of claim 1, wherein the oil-in-water emulsion comprises a terpenoid.
12. The method of claim 1, wherein the oil-in-water emulsion comprises a tocopherol.
13. The method of claim 1, wherein the oil-in-water emulsion comprises a polyoxyethylene sorbitan esters surfactant, an octoxynol surfactant, and/or a sorbitan ester.
14. The method of claim 1, wherein the oil-in-water emulsion comprises polysorbate 80.
15. The method of claim 1, wherein the oil-in-water emulsion comprises sorbitan trioleate.
16. The method of claim 1, wherein the oil-in-water emulsion comprises squalene.
17. The method of claim 1, wherein the oil-in-water emulsion comprises about 4.3% squalene by weight, about 0.5% polysorbate 80 by weight, and about 0.48% sorbitan trioleate by weight.
18. The method of claim 1, wherein the composition comprises 3-O-deacylated monophosphoryl lipid A.
19. The method of claim 1, wherein the composition is substantially free of thiomersal.
20. The method of claim 1, wherein the composition is substantially free of mercurial material.

* * * * *